US012630781B2

United States Patent
(12) United States Patent
Hoelscher et al.

(10) Patent No.: US 12,630,781 B2
(45) Date of Patent: May 19, 2026

(54) FRAGRANCE OR FLAVOUR MIXTURE

(71) Applicant: SYMRISE AG, Holzminden (DE)

(72) Inventors: Bernd Hoelscher, Halle (DE); Vijayanand Chandrasekaran, Holzminden (DE); Johannes Panten, Höxter (DE); Tobias Voessing, Beverungen (DE)

(73) Assignee: SYMRISE AG, Holzminden (DE)

(*) Notice: Subject to any disclaimer, the term of this patent is extended or adjusted under 35 U.S.C. 154(b) by 1219 days.

(21) Appl. No.: 17/611,886

(22) PCT Filed: May 17, 2019

(86) PCT No.: PCT/EP2019/062864
§ 371 (c)(1),
(2) Date: Nov. 16, 2021

(87) PCT Pub. No.: WO2020/233778
PCT Pub. Date: Nov. 26, 2020

(65) Prior Publication Data
US 2022/0228085 A1 Jul. 21, 2022

(51) Int. Cl.
*C11B 9/00* (2006.01)
*A23L 27/20* (2016.01)
(Continued)

(52) U.S. Cl.
CPC .............. *C11B 9/0019* (2013.01); *A61K 8/37* (2013.01); *A61Q 13/00* (2013.01); *C07C 67/08* (2013.01);
(Continued)

(58) Field of Classification Search
CPC ......... C11B 9/0019; A61K 8/37; A61Q 13/00; C07C 67/08; C07C 67/333; C07C 69/593;
(Continued)

(56) References Cited

U.S. PATENT DOCUMENTS 10,988,434 B2 * 4/2021 Chandrasekaran ... C07C 67/333

FOREIGN PATENT DOCUMENTS

JP H01104030 A * 4/1989
WO WO-2018114073 A1 * 6/2018 ......... A23L 27/2028

OTHER PUBLICATIONS

Mutsuji Sakai et al: "Studies of the Isomerization of Unsaturated Carboxylic Acids. N. Base-catalyzed Rearrangements of [beta],[gamma]-Unsaturated Esters to !'x'.lpha], [beta ]-Isomers", Bulletin of the Chemical Society of Japan, vol. 51, No. 10, 1978, pp. 2970-2972.*
(Continued)

*Primary Examiner* — Deborah D Carr
(74) *Attorney, Agent, or Firm* — MARSHALL, GERSTEIN & BORUN LLP

(57) ABSTRACT

Fragrance or flavour mixtures containing (i) (E)-2-methyl-but-2-endicarboxylic acid diesters, (ii) (Z)-2-methyl-but-2-endicarboxylic acid diesters and (iii) 2-methylenebutanedi-carboxylic acid diesters with a fruity, pear-like note are provided. Further provided are a process for the preparation of these fragrances or flavourings or fragrance or flavouring mixtures, and the use of the fragrance or flavouring mixtures to produce a fruity, pear-like fragrance or flavour or for the preparation of a fragrance mixture or a perfume oil, cosmetic
(Continued)

agent, application agent, detergent and cleaning agent, foodstuff, animal feed or pharmaceutical product, as well as the products made therefrom which contain the fragrance or flavouring mixtures in a sensory effective amount.

7 Claims, 3 Drawing Sheets

(51) Int. Cl.

| | |
|---|---|
| ***A23L 27/29*** | (2016.01) |
| ***A61K 8/37*** | (2006.01) |
| ***A61Q 13/00*** | (2006.01) |
| ***C07C 67/08*** | (2006.01) |
| ***C07C 67/333*** | (2006.01) |
| ***C07C 69/593*** | (2006.01) |
| ***C11D 3/20*** | (2006.01) |
| ***C11D 3/50*** | (2006.01) |

(52) U.S. Cl.
CPC .......... *C07C 67/333* (2013.01); *C07C 69/593* (2013.01); *C11D 3/2093* (2013.01); *C11D 3/50* (2013.01); *A23L 27/2024* (2016.08); *A23L 27/29* (2016.08); *A23V 2002/00* (2013.01)

(58) Field of Classification Search
CPC ..... C11D 3/2093; C11D 3/50; A23L 27/2024; A23L 27/29; A23L 27/2028; A23V 2002/00
See application file for complete search history.

(56) References Cited

OTHER PUBLICATIONS

Arctander, "Perfume and Flavor Chemicals," front matter and table of contents, self-publication (1969).
Enoki et al., "Chemical synthesis, iron redox interactions and charge transfer complex formation of alkylitaconic acids from Ceriporiopsis subvermispora," Chemistry and Physics of Lipids 120:9-20 (2002).
Ferraboschi et al., "Selective Enzymatic Transformations of Itaconic Acid Derivatives: An Access to Potentially Useful Building Blocks," Tetrahedron 50(10):3251-3258 (1994).
Fittig, "Condensation of aldehydes and lactones with dibasic acids," Justus Lieigs Annalen Der Chemie, DE, 331(2):151-196 (1904).
Sakai et al., "Studies of the Isomerization of Unsaturated Carboxylic Acids. IV> Base-catalyzed Rearrangements of β,γ-Unsaturated Esters to α,β-Isomers," Bulletin of the Chemical Society of Japan 51(10):2970-2972 (1978).
Sakai, "Studies of the Isomerization of Unsaturated Carboxylic Acids. III. Thermal Rearrangement of Dimenthyl Methylenesuccinate to Dimethyl Mesaconate," Bulletin of the Chemical Society of Japan 50(5):1232-1234 (1977).
Singer et al., "Isomerisations of Olefinic Carboxylic Acid Esters With Rhodium Complexes," Tetrahedron 28:5769-5777 (1972).
Surburg et al., "Common Fragrance and Flavor Materials," 6th Edition, front matter and table of contents, Wiley-VCH, Weinheim (2016).

* cited by examiner

Formula (I) (66 - 72 %),
(II) (4 - 6 %) and
(III) (22 - 27 %)

(Process according to the invention)

Formula (I) (84 - 90 %),
(II) (7 - 11 %) and (III) (1 - 3 %)

(State of the art)

FRAGRANCE OR FLAVOUR MIXTURE

CROSS-REFERENCE TO RELATED APPLICATIONS

This is a U.S. National Phase of International Application No. PCT/EP2019/062864, filed May 17, 2019, the contents of which are incorporated herein by reference.

FIELD OF THE INVENTION

The invention is in the field of fragrances and flavours and relates to fragrance or flavour mixtures with a fruity, pear-like note, a process for the production of fragrances or flavours or fragrance or flavour mixtures with a fruity, pear-like note, the use of these fragrances or flavour mixtures to produce a fruity, pear-like note or for the preparation of a perfume mixture, perfume oils, cosmetic products, application products, detergents and cleaning products, foodstuffs or animal feedstuffs, and the products made therefrom which contain the perfume or flavouring mixtures.

Despite a large number of existing fragrances or flavours, there is still a general need for new fragrances or flavours in the perfume industry. In particular, there is a need for fragrances or flavors that are not only characterized by new original fragrances, but also have additional positive secondary properties beyond their olfactory properties, such as higher stability and sufficiency under certain conditions of use, better adhesion, greater radiance, a lower odor threshold, or even better dermatological or toxicological properties, such as good biodegradability.

In particular, there is a need for fragrances or flavourings which, at a lower dosage, make an equal or greater contribution to fragrance or flavour than comparable substances and thus lead to a lower input into the environment (low volume-high impact), or which can be made available at a significantly lower cost for an equal contribution to fragrance. There is a particular need here for fragrances or flavors with complex odor or taste properties, such as fruity pear-like odor or taste properties. However, acetic acid amyl ester, which is otherwise known for its pear-like aroma, does not meet these conditions.

In addition, there is a need for fragrances or flavors that can be produced from natural or sustainably produced raw materials, for example from plant-based feedstock or bio-based raw materials, with a view to environmental protection, energy and resource efficiency.

There is an even greater need for fragrances or flavourings or mixtures of fragrances or flavourings that are free from the undesirable and harmful by-products that can arise in the synthesis of such fragrances.

WO 2018/114073 A1 discloses fragrances or fragrance mixtures and their applications, in particular perfume oils, cosmetic agents, application agents or detergents and cleaning agents, which comprise a sensory effective amount of (i) (E)-2-methyl-but-2-endicarboxylic acid diethyl ester, (ii) (Z)-2-methyl-but-2-endicarboxylic acid diethyl ester or (iii) 2-methylenebutanedicarboxylic acid diethyl ester or mixtures from these compounds or mixtures of derived analogous esters.

The fragrances are produced by applying a series of linear syntheses.

The first variant of the process for the preparation of a mono- and/or diester of mesaconic acid comprises the steps of (i) reacting itaconic acid with acetic anhydride to give itaconic anhydride;

(ii) Itaconic anhydride is isomerized to citraconic anhydride;

(iii) esterifying the citraconic anhydride with an aliphatic, araliphatic or aromatic alcohol having 1 to 10 carbon atoms or a diol having 1 to 5 hydroxyl groups to obtain a mono- and/or diester of the citraconic acid; and (iv) rearranging the mono- and/or diester of citraconic acid to a mono- and/or diester of mesaconic acid.

The second variant of the process for preparing a mono and/or diester of mesaconic acid comprises the steps of:

(i) providing a solution containing at least one mono- and/or diester of citraconic acid and optionally a solvent;

(ii) adding iodine to the solution;

(iii) heating the iodine-containing solution to about 170 to about 200° C.; and (iv) optionally purifying the resulting product by distillation.

Furthermore, it is preferred there that the second alternative manufacturing process is used as step (iv) in the first-mentioned manufacturing process. The last rearrangement step is thus carried out after the second alternative manufacturing process, as it were, following steps (i) to (iii) in the first-mentioned manufacturing process.

However, the above-mentioned synthesis methods have significant disadvantages when upscaled to industrial manufacturing production: they require several and longer synthesis steps, a longer reaction time and result in a low yield.

In addition, the use of halogen, particularly iodine, in the isomerization process requires higher amounts to complete the reaction. In addition, the fragrance mixture produced during synthesis is not free of by-products. Some of these by-products are undesirable because they have an adverse effect on the fragrance compounds. For example, the fragrance or flavour mixtures contain halogen, in particular iodine, which is used in the synthesis, in an amount well above the guideline value of 10 ppm. Iodine (HJ) also causes discoloration of the fragrance or flavoring mixtures, which is undesirable. The process therefore requires a further process step to separate the iodine from the fragrance or flavour mixture, for example by washing the fragrance or flavour mixture with sodium disulphite. Furthermore, another disadvantage of halogens is that they can attach to double bonds of fragrances or flavors. The attachment results in a change in the fragrance or flavour substances and thus in a deterioration of the odour profile. Furthermore, halogens may cause skin irritations, e.g. reddening of the skin.

Diesters of mesaconic acid with high purity can also be produced directly from mesaconic acid. However, mesaconic acid (purchased goods) is very expensive.

The task of the present invention has therefore been to provide fragrances and flavors or mixtures of fragrances or flavors with a fruity, pear-like aroma based on renewable raw materials, preferably waste materials, and which overcome the above-mentioned disadvantages of the prior art, namely which, on the one hand, can be produced with a shorter reaction time and thus with less technical effort and at lower cost and, on the other hand, have a high purity, i.e. are free from by-products, in particular are free from halogens.

SUMMARY OF THE INVENTION

A first object of the invention relates to a fragrance or flavour mixture comprising a sensory effective amount of the compounds of general formula (I), formula (II) and formula (III):

Formula (I)

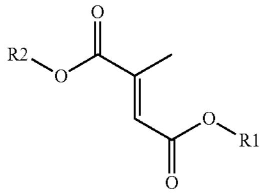

Formula (II)

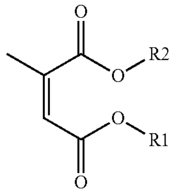

Formula (III)

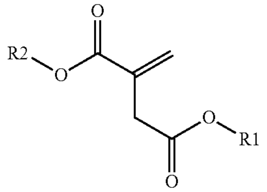

in which R1 in each case represents a linear, branched or cyclic alkyl radical having 1 to 10 carbon atoms, an araliphatic or aromatic radical, and/or in which R2 in each case represents a linear, branched or cyclic alkyl radical having 1 to 10 carbon atoms, an araliphatic or aromatic radical, and optionally one or more further constituents, in which the fragrance or flavour mixture is halogen-free, in particular iodine-free.

The second object of the present invention is a process for preparing a compound of the general formula (I), formula (II) or formula (III) or a mixture comprising one, two or three compounds selected from the group consisting of compounds of the general formula (I), formula (II) and formula (III), which comprises the following steps:

(a) esterification of itaconic acid with an alcohol selected from the group consisting of an aliphatic, araliphatic or aromatic alcohol having 1 to 10 carbon atoms and a polyol having 2 to 6 hydroxyl groups to obtain an itaconic acid diester; and (b) Isomerization of the itaconic diester with an organic nitrogenous base to obtain a compound of the general formula (I), formula (II) or formula (III) or a mixture comprising one, two or three compounds selected from the group consisting of compounds of the general formula (I), formula (II) and formula (III).

In a third aspect, the present invention relates to a fragrance or flavour of the general formula (I), formula (II) or formula (III) or to a fragrance or flavour mixture comprising one, two or three compound(s) from the group consisting of compounds of the general formula (I), formula (II) and formula (III) obtainable by the process according to the invention, the process being carried out in particular without the use of halogen-containing, in particular iodine-containing, reagents.

In a fourth aspect, the present invention relates to a method for imparting, modifying or enhancing a fruity, pear-like odor note in a fragrance blend, perfume oil, cosmetic product, applicator or detergent or for imparting, modifying or enhancing a fruity, pear-like flavor note in a food, animal feed or pharmaceutical product, comprising the steps of:

(i1) providing the fragrance or flavour mixture according to the invention; and (i2) mixing a sensory effective amount of the fragrance or flavour mixture sufficient to elicit a fruity, pear-like odour or flavour in the finished preparation with at least one further fragrance or flavour or a mixture of further fragrances or flavours; or (ii1) providing the fragrance or flavour mixture according to the invention; and (ii2) mixing a sensory effective amount of the fragrance or flavour mixture, sufficient to produce a fruity, pear-like odour or flavour in the finished preparation, with a perfume oil, cosmetic, applicator, detergent, food, animal feed or pharmaceutical product.

Another object of the present invention is the use of a sensory effective amount of the fragrance or flavor mixture according to the invention comprising the compounds of general formula (I), formula (II) and formula (III) for imparting, modifying or enhancing a fruity, pear-like odor or flavor note in a fragrance mixture, a perfume oil, cosmetic agent, an applicator or a detergent and cleaning product or for imparting, modifying or enhancing a fruity, pear-like flavour note in a foodstuff, animal feed or pharmaceutical product or for preparing a perfume mixture, a perfume oil, cosmetic agent, applicator, detergent and cleaning product, foodstuff, animal feed or pharmaceutical product.

Ultimately, in a further aspect, the present invention relates to a fragrance mixture or perfume oil, cosmetic agent, applicator, detergent, cleaning agent, foodstuff, animal feedstuff or pharmaceutical product comprising a sensory effective amount of the fragrance or flavour mixture according to the invention comprising the compounds of general formula (I), formula (II) and formula (III).

These and other aspects, features and advantages of the present invention will be apparent to those skilled in the art from a study of the following detailed description and claims. In this regard, any feature from one aspect of the invention may be used or substituted in another aspect of the invention. Furthermore, it is understood that the examples contained in the present application describe and illustrate the invention but do not limit it and, in particular, that the present invention is not limited to these examples.

All percentages are by weight unless otherwise stated. Numerical examples given in the form "from x to y" include the values given. When multiple preferred numeric ranges are given in this format, it is understood that all ranges created by combining the various endpoints are also included.

FIGURES

FIG. 1 schematically shows the process for the preparation of fragrances or flavors of the general formulae (I), (II) and (III) or the fragrance or flavor mixtures thereof with a fruity, pear-like note according to the present invention in comparison with the process for the preparation of the fragrances or flavors or fragrance or flavor mixtures with a fruity, pear-like note according to the prior art.

DETAILED DESCRIPTION OF THE INVENTION

Figure 1:
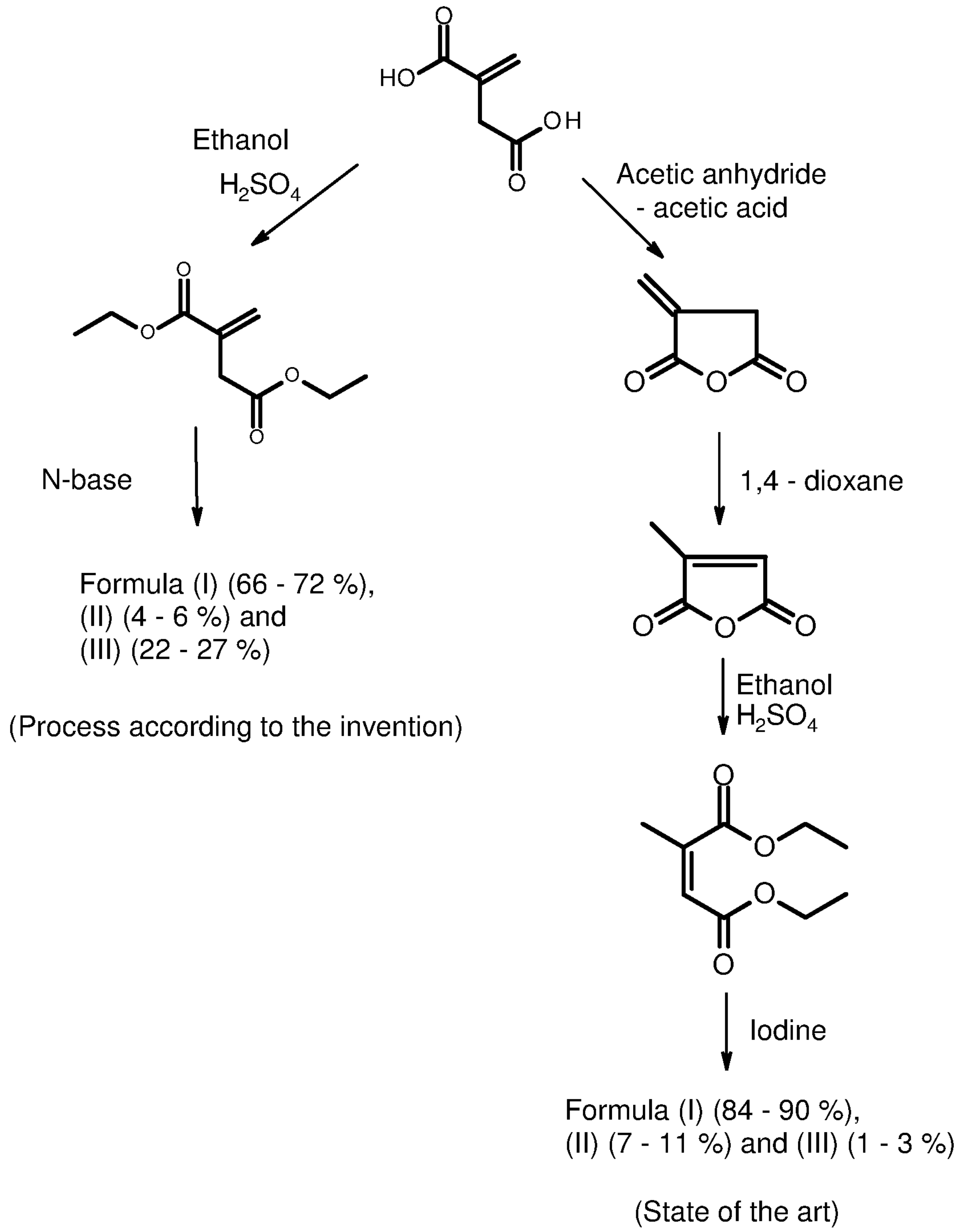
Figure 2:
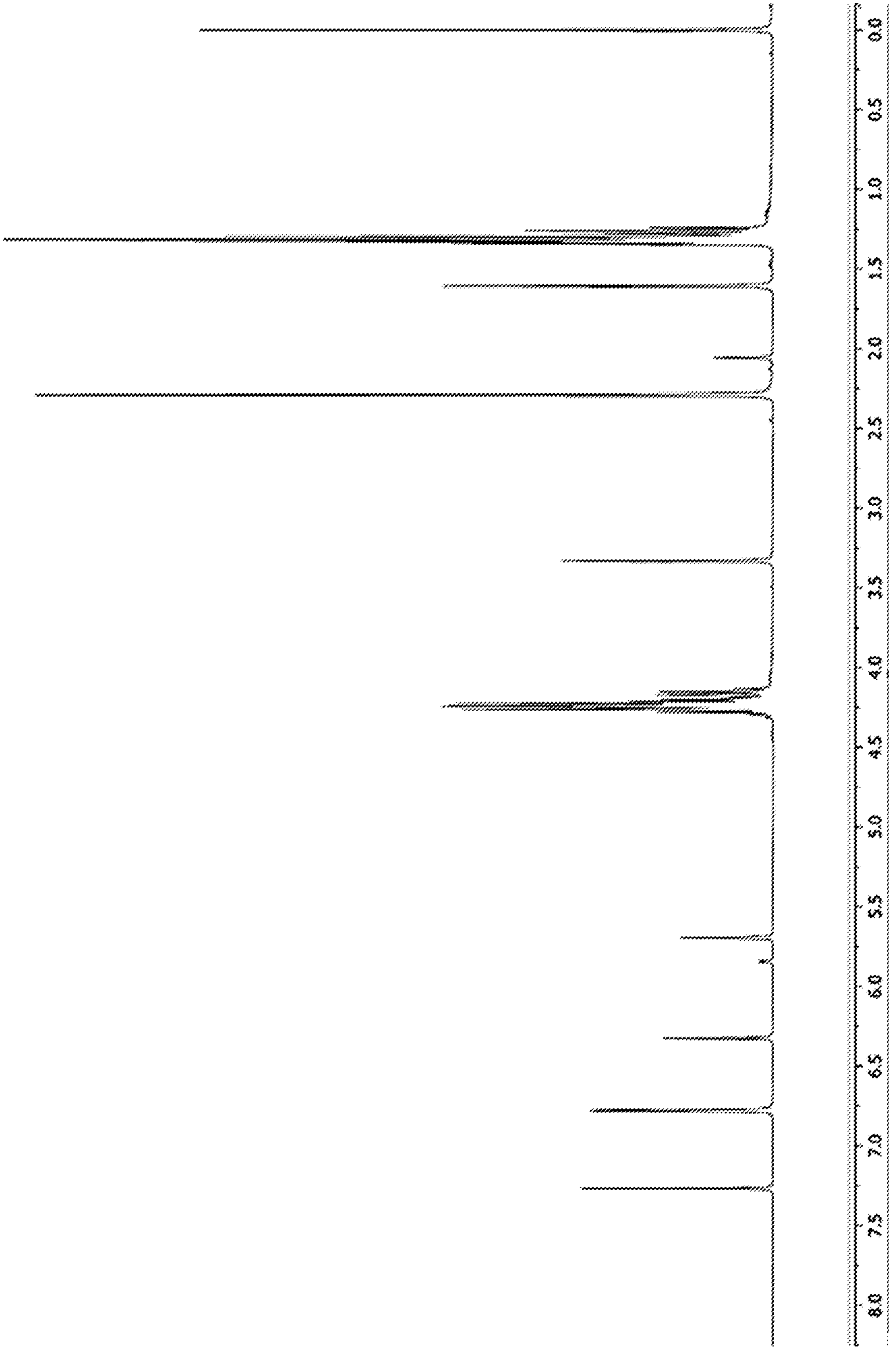
FIG. 2 shows the $^{1}H$-NMR-Spectrum (400 MHz, $CDCl_3$) of a fragrance or flavour mixture according to the invention. The scale is in f1 (ppm).
Figure 3:
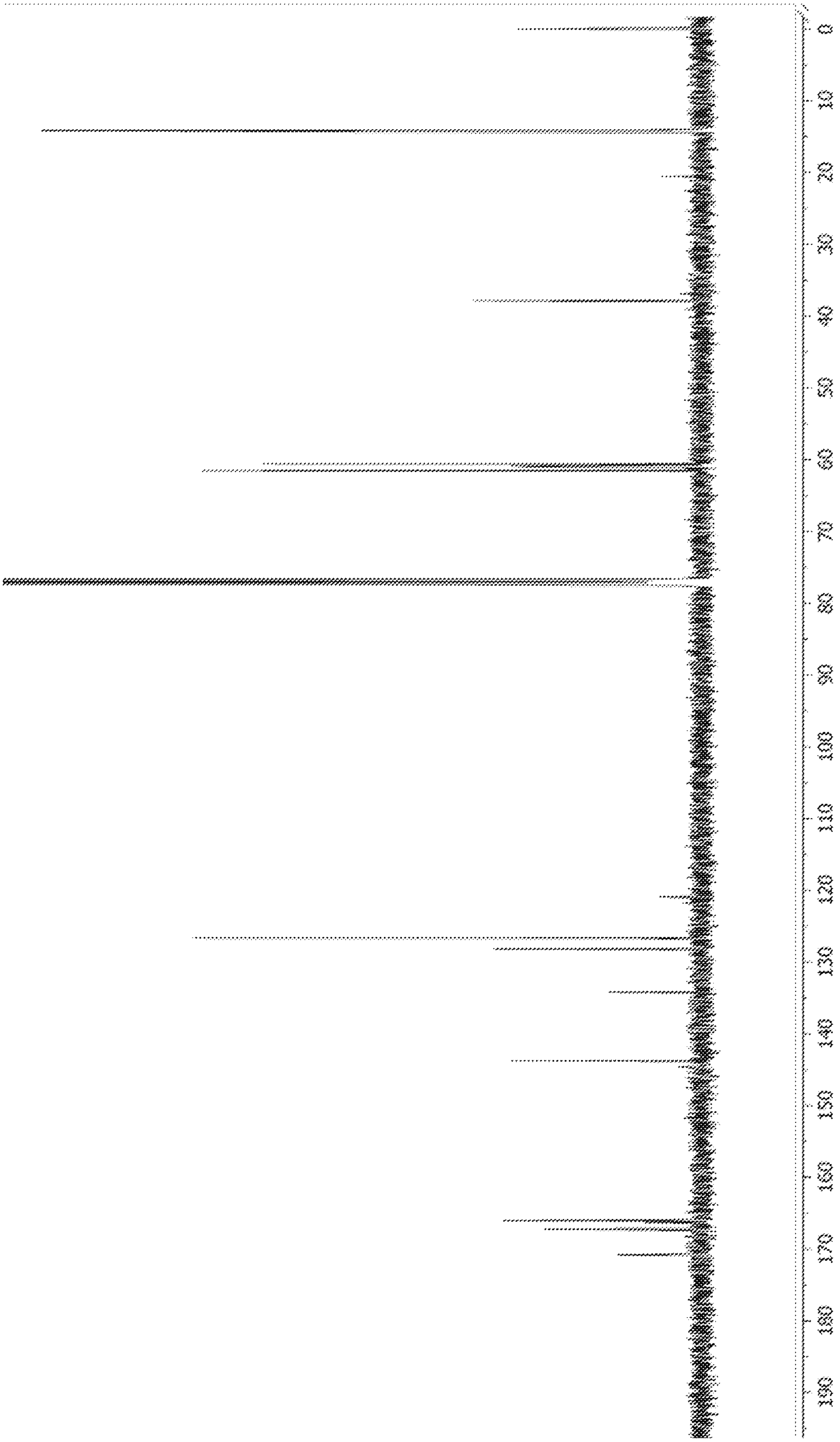
FIG. 3 shows the $^{13}C$-NMR-Spectrum (101 MHz, $CDCl_3$) of a fragrance or flavour mixture according to the invention. The scale is in f1 (ppm).

In a first aspect, the present invention relates to a fragrance or flavour mixture comprising a sensory effective amount of the compounds of general formula (I), formula (II) and formula (III):

Formula (I)

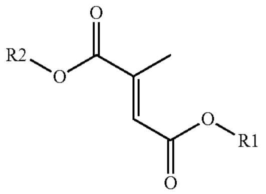

Formula (II)

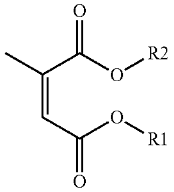

Formula (III)

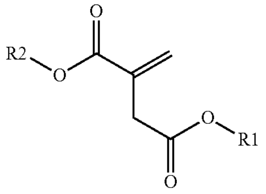

where R1 in each case represents a linear, branched or cyclic alkyl radical having 1 to 10 carbon atoms, an araliphatic or aromatic radical, and/or where R2 in each case represents a linear, branched or cyclic alkyl radical having 1 to 10 carbon atoms, an araliphatic or aromatic radical, and optionally one or more further constituents. The fragrance or flavouring mixture is characterised in that it is halogen-free, in particular iodine-free.

The compounds of the fragrance or flavour mixture according to the invention are preferably a mixture of isomers of

- derivatives of mesaconic acid ((E)-2-methyl-but-2-endicarboxylic acid) (compounds of general formula (I)),
- derivatives of citraconic acid ((Z)-2-methyl-but-2-endicarboxylic acid) (compounds of the general formula (II)), and
- derivatives of itaconic acid (2-methylenebutanedicarboxylic acid) (compounds of general formula (III).

Surprisingly, it was found that compounds of formula (I) in particular are suitable as fruity, pear-like fragrances or flavors and fully satisfy the complex requirement profile described at the beginning. The compounds of the formula (II) and of the formula (III) are also produced during the production and also exhibit a pear-like odor or aroma in a weakened form.

Due to their sensory properties, the fragrance or flavour mixtures according to the invention are equally suitable as a fragrance or olfactory substance on the one hand or as a flavour substance or aroma substance on the other hand. The terms “odor” and “flavor”, on the one hand, or “fragrance mixture” and “flavoring mixture”, on the other hand, are used equally alongside one another in the context of the present application and are therefore dependent on the intended use, namely fragrancing on the one hand or flavoring on the other hand.

The compounds of general formula (I), formula (II) and formula (III) are compounds prepared from itaconic acid. Itaconic acid ($C_5H_6O_4$) is an organic dicarboxylic acid. It is produced, among other things, during the distillation of citric acid. The technical production of itaconic acid is carried out biotechnologically by submerged fermentation of molasses (by-product of sugar production) and other substrates with strains of the fungi Aspergillusitaconicus or Aspergillusterreus. Thus, the compounds of the general formula (I), formula (II) and formula (III) can be produced from natural or sustainably produced raw materials.

It was also surprising that the compounds of the fragrance or flavour mixture according to the invention can be permanently and stably incorporated into a large number of different formulations and, in terms of their odour or flavour, qualitatively and quantitatively reach or even exceed the ethyl decadienoate standard.

A sensory effective amount is understood to be a proportion of the compounds of the general formula (I), formula (II) and formula (III) which is sufficient to evoke a fruity, pear-like odour or taste impression. This fruity, pear-like odor or taste impression is basically evoked when at least 0.001% by weight of the compounds of the general formula (I), formula (II) and formula (III) are present in the fragrance or flavoring mixture.

In a preferred embodiment, the present invention relates to a fragrance or flavor mixture comprising a sensory effective amount of the compounds of general formula (I), formula (II) and formula (III) selected from the group consisting of diesters of mesaconic acid, citraconic acid and itaconic acid.

Preferably, R1 and/or R2 in the compounds of the general formula (I), formula (II) or formula (III) each independently represent a linear or branched alkyl radical having 1 to 10 carbon atoms or a cyclic alkyl radical having 1 to 10 carbon atoms. The linear radicals are particularly preferred here, especially alkyl radicals having 1 to 4 carbon atoms. Alternatively preferred are branched alkyl radicals having this number of carbon atoms.

The residues R1 and R2 can be the same or different.

The group of preferred linear alkyl radicals for R1 and/or R2 having 1 to 10 carbon atoms in the compounds of general formula (I), formula (II) or formula (III) is formed by the following radical radicals: methyl, ethyl, n-propyl, n-butyl, n-pentyl, n-hexyl, n-heptyl, n-octyl, n-nonyl and n-decyl. Preferred linear alkyl radicals are methyl, ethyl, but also suitable are n-propyl, n-butyl, n-pentyl and n-hexyl. Particularly preferred among the linear alkyl radicals are methyl, ethyl, n-propyl and n-butyl. Most preferred is the alkyl radical ethyl.

The group of branched alkyl radicals for R1 and/or R2 having 1 to 10 carbon atoms in the compounds of the general formula (I), formula (II) or formula (III) is formed from: isopropyl, isobutyl, sec-butyl, tert-butyl, isopentyl, tert-pentyl, iso-hexyl, tert-hexyl, iso-heptyl, iso-octyl, tert-octyl, iso-nonyl, tert-nonyl, tert-decyl and iso-decyl. Preferred branched alkyl radicals are isopropyl, isobutyl, sec-butyl and tert-butyl. Particularly preferred branched alkyl radicals are isopropyl and isobutyl.

The group of cyclic alkyl radicals for R1 and/or R2 having 1 to 10 carbon atoms in the compounds of the general formula (I), formula (II) or formula (III) is formed from: cyclopropane, cyclobutane, cyclopentane, cyclohexane, cycloheptane and cyclooctane, cyclononane and cyclodecane. Preferred cyclic alkyl radicals are cyclopentane and cyclohexane.

In the group of araliphatic radicals for R1 and/or R2 in the compounds of the general formula (I), formula (II) or formula (III) preferred are alkyl radicals on which one or more hydrogen atom(s) is/are replaced by an aromatic radical. The group of araliphatic radicals in the compounds of general formulae (I), (II) or (III) is preferably formed from: toluene, 2-methylfuran, 3-methylfuran, picolines, cresols, xylenes, 1methylnaphthalene-, 2-methylnaphthalene and ethylbenzene. Preferred araliphatic radicals are toluene and ethylbenzene.

The group of aromatic radicals for R1 and/or R2 in the compounds of the general formula (I), formula (II) or formula (III), formula (I), formula (II) or formula (III) is preferably formed from: pyrimidines, furan, thirane, benzene, naphthalene, phenol, pyridine and benzodiazepines. Preferred aromatic radicals are furan and benzene.

In a preferred variant of the present invention, the radicals R1 and/or R2 in the compounds of the general formula (I), formula (II) or formula (III) in the fragrance or flavour mixture described above each independently represent a C1 to C4 radical, i.e. in particular a methyl, ethyl, propyl or butyl radical. These compounds are particularly easy to prepare and exhibit the most impressive odor profiles.

In an alternative preferred embodiment of the present invention, the radical R1 in the compounds of the general formulae (I), (II) and (III) in the fragrance or flavour mixture described above is a methyl, ethyl, propyl, and/or butyl radical, and the radical R2 in the compounds of the general formula (I), formula (II) or formula (III) in the fragrance or flavour mixture described above is a methyl radical or ethyl radical.

In another alternative embodiment of the present invention, the R2 radical in the compounds of the general formula (I), formula (II) or formula (III) in the fragrance or flavour mixture described above is a methyl, ethyl, propyl, and butyl radical, and the R1 radical in the compounds of the general formula (I), formula (II) or formula (III) in the fragrance or flavour mixture described above is a methyl radical or ethyl radical.

In another still more preferred variant of the present invention, the radicals R1 and R2 in the compounds of the general formula (I), formula (II) or formula (III) in the fragrance or flavour mixture described above are each the same radicals. This simplifies the preparation.

In a further variant of the present invention, the R1 and R2 radicals in the compounds of general formula (I), formula (II) or formula (III) in the fragrance or flavour mixture described are each independently selected from the group formed by: linear or branched methyl, ethyl, propyl and butyl radicals. In particular, the linear alkyl radicals and shorter branched alkyl radicals are suitable to fit into the odor binding pockets.

In further preferred embodiments of the present invention, the R1 and R2 radicals in the compounds of general formula (I), formula (II) or formula (III) in the fragrance composition described above are each independently methyl, ethyl, propyl or butyl radicals.

In a still more preferred further embodiment, the radicals R1 and R2 in the compounds of the general formula (I), formula (II) and formula (III) are each the same.

In another, even more preferred embodiment, the present invention relates to a fragrance or flavor blend comprising a sensory effective amount of compounds (I), (II) and (III) selected from the group consisting of:

(I) Mesaconic diester, (II) citraconic acid diesters, and (III) Itaconsäuredieester, wherein the diesters are preferably selected from the group consisting of dimethyl ester, diethyl ester, dibutyl ester or dipropyl ester, in particular diethyl ester.

Of the compounds of the general formula (I), formula (II) or formula (III) of the fragrance or flavoring mixture according to the invention, the compounds of the general formula (I) are particularly preferred, since they are characterized by a particularly intense fruity and pear-like odor or taste. The compounds of the general formula (II) (citraconic diesters) and (III) (itaconic diesters), are generally obtained together with the mesaconic diester as a mixture of isomers in the preparation of the fragrance or flavoring mixture, but are less intense in odor or taste than the mesaconic diesters and therefore have only a subordinate influence on the overall odor or overall taste of the fragrance or flavoring mixture according to the invention.

In another most preferred embodiment, the present invention relates to a fragrance or flavor blend comprising a sensory effective amount of compounds of the general formulae (I), (II) and (III) selected from the group consisting of:

(I) diethyl (E)-2-methylbut-2-endioate (mesaconic acid diethyl ester), (II) diethyl (Z)-2-methylbut-2-endioate (citraconic acid diethyl ester), and (III) diethyl 2-methylene butanedioate (itaconic acid diethyl ester).

The three previously mentioned compounds (I), (II) and (III) represent respectively the most preferred variants of the general formulae (I), (II) and (III) of the fragrance or flavour mixture according to the invention, but the methyl esters, butyl esters or propyl esters are also favourable. A combination of ethyl esters, methyl esters and/or propyl esters of the compounds of the general formula (I), formula (II) or formula (III) is also possible.

Of the compounds of the general formula (I), formula (II) or formula (III) of the fragrance or flavoring mixture according to the invention, the substance diethyl (E)-2-methylbut-2-endioate or (E)-2-methylbut-2-endicarboxylic acid diethyl ester, in which, in the general formula (I), R1 and R2 represent an ethyl radical, and which is represented by the formula (IV)

(IV)

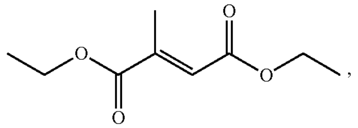

which is also known as mesaconic acid diethyl ester, is of particular importance to the invention and as such is already known from the literature. In this regard, reference is made to the following citations: Advanced Synthesis & Catalysis, 2012, 354 (14-15), 2859-2864; Organic Letters, 2008; 10(21), 4815-4818; Organic & Biomolecular Chemistry, 2010, 8(19), 4444-4450; Journal of American Chemical Society, 2005, 127(15), 5518-5527; Tetrahedron Letters, 1996, 37(5), 629-632; Tetrahedron Letters, 1983, 39(9), 1475-1485; Journal of American Chemical Society, 2015, 137(26), 8556-8563; Organic Letters, 2011; 13(7), 1884-1887; Australian Journal of Chemistry, 1984, 37(2), 417-

424; Tetrahedron Letters, 1981, 22(5), 381-384; Synthetic Communications, 1977, 7(6), 375-382; Helvetica Chimica Acta, 1974, 57(3), 856-863.

In the following, the designations diethyl (E)-2-methylbut-2-endioate or (E)-2-methylbut-2-endicarboxylic acid diethyl ester and mesaconic acid diethyl ester are used synonymously. The compound diethyl (E)-2-methylbut-2-endioate is characterized by a particularly intense fruity, pear-like odor or taste.

Particularly preferred for the compound of the general formula (II) is diethyl (Z)-2-methylbut-2-endioate or (Z)-2-methylbut-2-endicarboxylic acid diethyl ester (citraconic acid diethyl ester) and for the compound of the general formula (III) is diethyl 2-methylenebutanedioate or 2-methylene-butanedicarboxylic acid diethyl ester (itaconic acid diethyl ester), which together with the diethyl (E)-2-methylbutanedioate or mesaconic acid diethyl ester give a preferred perfume mixture.

The aforementioned compounds of the general formula (II) diethyl (Z)-2-methylbut-2-endioate and of the general formula (III) diethyl 2-methylene-butanedioate, are generally obtained together with the mesaconic acid diethyl ester as a mixture of isomers during the preparation of the fragrance or flavoring mixture, but are less intense in odor or taste than the mesaconic acid diethyl ester and therefore have only a subordinate influence on the overall odor or overall taste of the fragrance or flavoring mixture according to the invention.

Preferred are fragrance or flavoring mixtures or mixtures of isomers according to the invention comprising the compound of formula (I) in an amount of at least 50 to 100% by weight, more preferably from 60 to 78% by weight, most preferably from 66 to 72% by weight, the compound of formula (II) in an amount of at least 2 to 8% by weight, more preferably from 3 to 7% by weight and most preferably from 4 to 6% by weight, and the compound of formula (III) in an amount of at least 18 to 31% by weight, more preferably from 20 to 29% by weight and most preferably from 20 to 29% by weight and most preferably from 4 to 6% by weight, and the compound of the formula (III) in an amount of at least from 18 to 31% by weight, even more preferably from 20 to 29% by weight and most preferably from 22 to 27% by weight, based on the sum of the compounds of the general formulae (I), (II) and (III) or based on the total weight of the isomer mixture. This also applies to the particularly preferred compounds of the respective dimethyl esters, diethyl esters, dipropyl esters and dibutyl esters, and in particular to the diethyl esters of mesaconic acid, citraconic acid and itaconic acid.

Most preferred, therefore, are fragrance or flavoring mixtures or mixtures of isomers according to the invention which comprise diethyl (E)-2-methylbut-2-endioate or mesaconic acid diethyl ester (compound of formula (I)) in an amount of at least from 50 to 100% by weight, still more preferably from 60 to 78% by weight, most preferably from 66 to 72% by weight.% by weight, more preferably from 60 to 78% by weight, most preferably from 66 to 72% by weight, diethyl (Z)-2-methylbut-2-endioate (compound of formula (II)) in an amount of at least from 2 to 8% by weight, still more preferably from 3 to 7% by weight and most preferably from 4 to 6% by weight, and diethyl 2-methylene butanedioate (compound of the formula (III)) in an amount of at least from 18 to 31% by weight, still more preferably from 20 to 29% by weight and most preferably from 22 to 27% by weight, based on the sum of the compounds of the general formulae (I), (II) and (III) or based on the total weight of the isomer mixture.

In a preferred variant of the invention, the compound of formula (I) is present in the fragrance or flavour mixture in a ratio of 3:1, preferably in a ratio of 2.5:1, even more preferably in a ratio of 1.5:1, to the sum of the two compounds of formula (II) and formula (III). These ratios also preferably apply to the compound mixture of diethyl (E)-2-methylbut-2-endioate or mesaconic acid diethyl ester to diethyl (Z)-2-methylbut-2-endioate (citraconic acid diethyl ester) and diethyl 2-methylene butanedioate (itaconic acid di-ethyl ester).

In a further preferred variant of the invention, the ratio of the compound of formula (I) to the compound of formula (II) is in a range from 66:6 to 72:4. In this range, particularly good sensory results are obtained.

The sensory effects are most pronounced when diethyl (E)-2-methylbut-2-endioate and diethyl (Z)-2-methylbut-2-endioate are present in the fragrance or flavour mixture according to the invention in a ratio ranging from 66:6 to 72:4.

The proportion of the compound of the formula (II) (diester of citraconic acid, in particular diethyl ester of citraconic acid) and of the compound of the formula (III) (diester of itaconic acid, in particular diethyl ester of itaconic acid) which occurs together with the compound of the formula (I) (diester of mesaconic acid, in particular mesaconic acid diethyl ester) as a mixture of isomers during the preparation of the fragrance or flavouring mixture according to the invention, plays a subordinate role for the odour or taste of the fragrance or flavouring mixture, since the compounds of the general formulae (II) and (III) have a weaker pear-like odour or a weaker pear-like taste or a weaker pear-like aroma than the compounds of the general formula (I). The proportion of the compounds of the general formulae (II) and (III) in the fragrance or flavour mixture according to the invention therefore has only a subordinate influence on the overall odour or overall flavour of the fragrance or flavour mixture, which is shaped in particular by the proportion of compound of formula (I). A change, i.e. an increase, in the proportion of the compounds of formulae (II) and (III) in relation to the compound of formula (I) therefore also does not lead to a change, i.e. an intensification, of the odour or taste. At higher proportions of the mesaconic acid diester, in particular the mesaconic acid diethyl ester, (compound of formula (I)), which can ultimately be achieved by a high yield in the preparation, a stronger pear smell or pear taste is produced. A higher proportion of the mesaconic acid diester, in particular the mesaconic acid diethyl ester, (compound of formula (I)) in the mixture according to the invention can also be achieved, for example, by concentration.

The fragrance or flavoring mixture according to the present invention is characterized by a high purity, that is, it does not contain impurities and by-products formed during the synthesis of the compounds of general formula (I), formula (II) or formula (III).

According to the invention, the compounds of general formula (I), formula (II) and formula (III) have a purity of at least 98.0%, preferably a purity of 100%. In particular, mesaconic acid diethyl ester has a purity of at least 98.0%, but more preferably a purity of 100.0%. A fragrance or flavoring composition comprising pure or nearly pure mesaconic acid diethyl ester exhibits a particularly strong odor with a pear note.

The fragrance or flavour mixture according to the present comprises or consists of compounds of the general formulae (I), (II) and (III) in a sensory effective amount.

A sensory effective amount means a proportion of the compounds of the general formulae (I), (II) and formula (I) which is sufficient to evoke a fruity, pear-like odour or taste.

In a preferred further development of the present invention, the compounds of the general formula (I), formula (II) and formula (III) are present in the fragrance or flavoring mixture in an amount of from 0.001 to 99.999% by weight together, based on the total weight of the fragrance or flavoring mixture. This applies in particular to the particularly preferred dimethyl esters, diethyl esters, dipropyl esters or dibutyl esters of the compounds of the general formula (I), formula (II) and formula (III).

Even more preferably, the compounds of the general formula (I), formula (II) and formula (III) are present in the fragrance or flavoring mixture in an amount of from 0.05 to 50% by weight together, based on the total weight of the fragrance or flavoring mixture. This applies in particular to the particularly preferred dimethyl esters, diethyl esters, dipropyl esters or dibutyl esters of the compounds of the general formula (I), formula (II) and formula (III).

In an alternatively preferred embodiment of the present invention, the compounds of the general formula (I), formula (II) and formula (III), in particular the diemethyl esters, diethyl esters, dibutyl esters or dipropyl esters, are present in the fragrance or flavoring mixture in an amount of from 0.5 to 30% by weight together, based on the total weight of the fragrance or flavoring mixture.

In a particularly preferred embodiment of the present invention, the fragrance or flavor blend comprises diethyl (E)-2-methylbut-2-endioate or the mesaconic acid diethyl ester in admixture with diethyl (Z)-2-methylbut-2-endioate (citraconic acid diethyl ester) and diethyl 2-methylene butanedioate (itaconic acid diethyl ester), in an amount totaling from about 0.001 to about 99.999 wt. %, preferably in an amount of about 0.01 to about 90% by weight, preferably in an amount of about 0.05 to about 50% by weight and particularly preferably in an amount of about 0.5 to about 30% by weight.

The fragrance or flavor blend according to the present invention is characterized by an intense fruity, pear-like fragrance or flavor note and more volume, which is qualitatively and quantitatively equivalent to or even exceeds the ethyl decadienoate standard, as shown in Table 2 below.

It is of further advantage that the fragrance or flavour mixture according to the present invention does not contain any halogen impurities or halogen by-products, in particular no iodine impurities or iodine by-products, no halogen reagents, in particular no iodine reagents used in the prior art process, are used in its preparation. Such impurities or by-products may cause discoloration or adversely affect the fragrances, as described in detail above in the introductory part. As a result, the fragrance mixtures according to the invention are also more skin-compatible and do not cause reddening of the skin.

In addition to the special olfactory advantages described above, mention should also be made of the excellent material properties, such as solubility in customary cosmetic solvents, compatibility with other constituents of such products and the toxicological harmlessness of the compounds of the general formula (I), formula (II) and formula (III) of the fragrance or flavouring mixture according to the invention, which underline the special suitability for the purposes of use mentioned.

Another advantage over conventional and comparable fragrances or flavourings is their very favourable availability and simpler and therefore cheaper production.

The fragrance or flavour mixture according to the invention may preferably contain, in addition to the compounds of general formula (I), formula (II) and formula (III) as described above, one or more further (customary) active ingredients or functional ingredients, also one or more further fragrances not meeting the criteria of the compounds of general formulae (I), (II) and (III), which together make up 100% by weight in the fragrance or flavour mixture.

Fragrance or flavoring mixtures according to the invention can be used in liquid form undiluted or diluted with a solvent for perfuming or flavoring. Suitable and preferred solvents for this purpose are in particular ethanol, glycerol, 1,2-propylene glycol, 1,2-butylene glycol, dipropylene glycol, diethyl phthalate, triethyl citrate, isopropyl myristate and triacetin.

Such fragrance or flavour mixtures contain up to 90% by weight, preferably about 5% to about 70% by weight, in particular about 10% to about 50% by weight and particularly preferably about 15% to about 25% by weight of said solvents.

In a preferred alternative, the fragrance or flavour mixtures according to the invention comprise synthetic or natural carrier substances, preferably neutral in taste and odour, in particular carrier oils, which contain the fragrances in highly concentrated form and optionally perfumery solvents and/or excipients.

For some applications, it is also advantageous to adsorb the fragrance or flavoring compositions of the invention to a carrier that provides both a fine distribution of the fragrance materials therein in the product and a controlled release upon application. Such carriers may be porous inorganic materials such as light sulfate, silica gels, zeolites, gypsums, clays, clay granules, aerated concrete, etc., or organic materials such as woods, cellulose-based materials, sugars, dextrins (e.g., maltodextrin) or plastics such as PVC, polyvinyl acetates or polyurethanes. The combination of the fragrance mixture and carrier according to the invention represents an exemplary product according to the invention.

In an alternative preferred embodiment, the fragrance or flavour mixtures according to the invention are present in microencapsulated or spray-dried form or are present as inclusion complexes or as extrusion products, in order to be added in this form, for example, to a product to be perfumed or flavoured.

The microencapsulation of the fragrance or flavouring compositions according to the invention can be carried out, for example, by the so-called coacervation process using capsule materials made, for example, of polyurethane-like substances or soft gelatine. The spray-dried fragrance or flavorant compositions may be prepared, for example, by spray-drying an emulsion or dispersion comprising the fragrance or flavorant mixture according to the invention, wherein modified starches, proteins, dextrin and vegetable gums may preferably be used as carriers. Inclusion complexes can be prepared, for example, by incorporating dispersions of a fragrance mixture according to the invention and cyclodextrins or urea derivatives in a suitable solvent, for example water. Extrusion products can be obtained by fusing a fragrance or flavour mixture according to the invention with a suitable waxy substance and by extrusion followed by solidification, optionally in a suitable solvent, e.g. isopropanol.

If necessary, the properties of fragrance or flavour mixture preparations modified in this way can be further optimised by so-called "coating" with suitable materials with a view to a more specific release of fragrance, for which purpose waxy plastics such as, for example, polyvinyl alcohol are preferably used.

The fragrance or flavour mixtures according to the present invention advantageously contain at least one further fragrance or flavour or aroma, i.e. two, three, four, five or even far more further fragrance or flavour components, respectively consist of the isomer mixture of the compounds of the general formula (I), formula (II) and formula (III) according to the present invention, and here in particular diethyl (E)-2-methylbut-2-endioate, diethyl (Z)-2-methylbut-2-endioate and diethyl 2-methylene-butanedioate, in a sensory effective amount with at least one further fragrance or flavouring substance or substances. Typically, fragrances or flavors are not used in binary or ternary mixtures, but as components of sophisticated complex mixtures which may contain two, three, four, five, ten, or preferably even a much higher number of fragrances or flavors, in some cases in very small amounts, in order to provide a particularly rounded odor profile. The present mixtures of the invention are also to be understood in this sense, namely as a mixture of the isomer mixture of the compounds of the general formula (I), formula (II) and formula (III) with one, two, three, four, five, ten, but preferably an even far higher number of fragrances or flavours.

In a preferred further embodiment of the present invention, the described fragrance or flavor mixture therefore contains any desired number of further fragrances or flavors selected from the group formed by: (1) hydrocarbons; (2) aliphatic alcohols; (3) aliphatic aldehydes and their acetals; (4) aliphatic ketones and their oximes; (5) aliphatic sulfur-containing compounds; (6) aliphatic nitriles; (7) esters of aliphatic carboxylic acids; (8) acyclic terpene alcohols; (9) acyclic terpene aldehydes and ketones; (10) cyclic terpene alcohols; (11) cyclic terpene aldehydes and ketones; (12) cyclic alcohols; (13) cycloaliphatic alcohols; (14) cyclic and cycloaliphatic ethers; (15) cyclic and macrocyclic ketones; (16) cycloaliphatic aldehydes; (17) cycloaliphatic ketones; (18) esters of cyclic alcohols; (19) esters of cycloaliphatic alcohols; (20) esters of cycloaliphatic carboxylic acids; (21) araliphatic alcohols; (22) esters of araliphatic alcohols and aliphatic carboxylic acids; (23) araliphatic ethers; (24) aromatic and araliphatic aldehydes; (25) aromatic and araliphatic ketones; (26) aromatic and araliphatic carboxylic acids and esters thereof; (27) nitrogen-containing aromatic compounds; (28) phenols, phenyl ethers and phenyl esters; (29) heterocyclic compounds; (30) lactones; and any mixtures thereof.

The selection of fragrances or flavors is very comprehensive in this respect; corresponding substances with which the compound according to the invention can be advantageously combined from the compounds of the general formula (I), formula (II) and formula (III) can be found, for example, in "S. Arctander, Perfume and Flavor Chemicals, Volumes I and II, Montclair, N. J., 1969, self-published" or "H. Surburg and J. Panten, Common Fragrance and Flavor Materials, 6th edition, Wiley-VCH, Weinheim, 2016" and which are not already part of the mixture of the compounds of the general formula (I), formula (II) and formula (III) according to the invention.

The following may be mentioned in detail:

Extracts from natural raw materials: This group represents essential oils, concretes, absolues, resins, resinoids, balsams, tinctures such as ambergris tincture; Amyris oil; Angelica seed oil; Angelica root oil; Anise oil; Valerian oil; Basil oil; Tree moss absolue; Bay oil; Mugwort oil; Benzoeresin; Bergamot oil; Beeswax absolue; Birch tar oil; Bitter almond oil; Savory oil; Bucco leaf oil; Cabreuva oil; Cade oil; Calmus oil; Camphor oil; Cananga oil; Cardamom oil; Cascarilla oil; Cassia oil; Cassie-absolue; Castoreum-absolue; Cedar leaf oil; Cedarwood oil; Cistus oil; Citronella oil; Citron oil; Copaiva balsam; Copaiva balsam oil; Coriander oil; Costus root oil; Cumin oil; Cypress oil; Davana oil; Dill herb oil; Dill seed oil; Eau de brouts absolute; Oak moss absolute; Elemi oil; Tarragon oil; Eucalyptus citriodora oil; Eucalyptus oil; Fennel oil; Spruce needle oil; Galbanum oil; Galbanum resin; Geranium oil; Grapefruit oil; Guaiac wood oil; Gurjun balsam; Gurjun balsam oil; Helichrysum absolute; Helichrysum oil; Ginger oil; Iris root absolute; Iris root oil; Jasmine absolute; Calamus oil; Camomile oil blue; Camomile oil Roman; Carrot seed oil; Cascarilla oil; Pine needle oil; Curly mint oil; Caraway seed oil; Labdanum oil; Labdanum absolute; Labdanum resin; Lavandin absolute; Lavandin oil; Lavender absolute; Lavender oil; Lemongrass oil; Lovage oil; Lime oil distilled; Lime oil pressed; Linaloe oil; Litsea cubeba oil; Bay leaf oil; Mace oil; Marjoram oil; Mandarin oil; Masso bark oil; Mimosa absolue; Musk grain oil; Musk tincture; Muscat oil; Myrrh absolute; Myrrh oil; Myrtle oil; Clove leaf oil; Clove flower oil; Neroli oil; Olibanum absolute; Olibanum oil; Opopanax oil; Orange flower absolute; Orange oil; Origanum oil; Palmarosa oil; Patchouli oil; Perilla oil; Perubalsam oil; Parsley leaf oil; Parsley seed oil; Petitgrain oil; Peppermint oil; Pepper oil; Allspice oil; Pine oil; Poley oil; Rose absolue; Rosewood oil; Rose oil; Rosemary oil; Sage oil Dalmatian; Sage oil Spanish; Sandalwood oil; Celery seed oil; Spicy lavender oil; Star anise oil; Styrax oil; Tagetes oil; Fir needle oil; Tea tree oil; Turpentine oil; thyme oil; tolu balsam; tonka absolute; tuberose absolute; vanilla extract; violet leaf absolute; verbena oil; vetiver oil; juniper berry oil; wine yeast oil; wormwood oil; wintergreen oil; ylang oil; hyssop oil; civet absolute; cinnamon leaf oil; cinnamon bark oil; and fractions thereof, or ingredients isolated therefrom.

Single fragrances: Single fragrances can be divided into a variety of classes, namely:

Hydrocarbons, such as 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

Aliphatic alcohols such as hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxy octan-2-ol; 9-decenol; 10-undecenol; 4-methyl-3-decen-5-ol;

Aliphatic aldehydes and their acetals such as hexanal; heptanal; octanal; nonanal; decanal; undecanal; dodecanal; tridecanal; 2-methyloctanal; 2-methyl-nonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptamethyl acetal; 1,1-dimethoxy-2,2,5-trimethyl-4-hexene; citronellyloxyacetaldehyde; 1-(1-methoxy-propoxy)-(E,Z)-3-hexene;

Aliphatic ketones and their oximes such as 2-heptanone; 2-octanone; 3-octanone; 2-nonanone; 5-methyl-3-heptanone; 5-methyl-3-heptanonoxime; 2,4,4,7-tetramethyl-6-octen-3-one; 6-methyl-5-hepten-2-one;

Aliphatic sulfur-containing compounds such as 3-methylthiohexanol; 3-methylthiohexyl acetate; 3-mercaptohexanol; 3-mercaptohexyl acetate; 3-mercapto-hexyl butyrate; 3-acetylthiohexyl acetate; 1-menthen-8-thiol;

Aliphatic nitriles such as 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

Esters of aliphatic carboxylic acids such as (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methyl pentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxyacetate; methyl 3,7-dimethyl-2,6-octadienoate; 4-methyl-2-pentyl crotonate;

Acyclic terpene alcohols such as citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and their formates, acetates, propionates, isobutyrates, butyrates, isovalerianates, pentanoates, hexanoates, crotonates, tiglinates and 3-methyl-2-butenoates;

Acyclic terpene aldehydes and ketones such as geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethylacetals of geranial, neral, 7-hydroxy-3,7-dimethyloctanal;

Cyclic terpene alcohols such as menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiaol; and their formates, acetates, propionates, isobutyrates, butyrates, isovalerianates, pentanoates, hexanoates, crotonates, tiglinates and 3-methyl-2-butenoates;

Cyclic terpene aldehydes and ketones such as menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-Trimethyl-2-cyclohexen-1-yl)-2-buten-1-on; 1,3,4,6,7,8a-Hexahydro-1,1,5,5-tetramethyl-2H-2,4a-methanonaphthalen-8(5H)-on; 2-Methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (methylcedrylketone);

Cyclic alcohols such as 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

Cycloaliphatic alcohols such as alpha,3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-Methyl-5-(2,2,3-trimethyl-3-cyclopent-1-yl)-pentan-2-ol; 3-Methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

Cyclic and cycloaliphatic ethers such as cineol; cedryl methyl ether; cyclododecyl methyl ether; 1,1-dimethoxycyclododecane; (ethoxymethoxy)cyclododecane; alpha-cedrene epoxide; 3a,6,6,9a tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]tri-deca-4,8-diene; rose oxide; 2-(2,4-dimethyl-3-cyclohexen-1-yl)-5-methyl-5-(1-methylpropyl)-1,3-dioxane;

Cyclic and macrocyclic ketones such as 4-tert.butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 9-cyclohepta decen-1-one; cyclopentadecanone; cyclohexadecanone;

Cycloaliphatic aldehydes such as 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

Cycloaliphatic ketones such as 1-(3,3-Dimethylcyclohexyl)-4-penten-1-on; 2,2-Dimethyl-1-(2,4-dimethyl-3-cyclohexen-1-yl)-1-propanon; 1-(5,5-Dimethyl-1-cyclo hexen-1-yl)-4-penten-1-on; 2,3,8,8-tetramethyl-1,2,3,4,5,6,7,8-octahydro-2-naphtalenyl methyl ketone; methyl-2,6,10-trimethyl-2,5,9-cyclododecatrienyl ketone; tert.-butyl-(2,4-dimethyl-3-cyclohexen-1-yl)ketone;

Esters of cyclic alcohols such as 2-tert-butyl cyclohexyl acetate; 4-tert-butyl cyclo hexyl acetate; 2-tert-pentyl cyclohexyl acetate; 4-tert-pentyl cyclohexyl acetate; 3,3,5-trimethyl cyclohexyl acetate; decahydro-2-naphthyl acetate; 2-cyclopentylcyclo-pentylcrotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5, resp. 6-indenyl acetate; 4,7-methano-3a,4,5,6,7,7a-hexahydro-5, or 6-indenyl propionate; 4,7-methano-3a,4,5,6,7,7a-hexahydro-5, or 6-indenyl isobutyrate; 4,7-methano-octahydro-5, or 6-indenyl acetate;

Esters of cycloaliphatic alcohols such as 1-cyclohexylethyl crotonate;

Esters of cycloaliphatic carboxylic acids such as alyl 3-cyclohexyl propionate; allyl cyclohexyloxy acetate; cis- and trans-methyl dihydrojasmonate; cis- and trans-methyl jasmonate; methyl 2-hexyl-3-oxocyclopentane carboxylate; ethyl 2-ethyl-6,6-dimethyl-2-cyclohexene carboxylate; ethyl 2,3,6,6-tetramethyl-2-cyclohexene carboxylate; ethyl 2-methyl-1,3-dioxolane-2-acetate;

Araliphatic alcohols such as benzyl alcohol; 1-phenylethyl alcohol; 2-phenyl ethyl alcohol; 3-phenyl propanol; 2-phenyl propanol; 2-phenoxyethanol; 2,2-dimethyl-3-phenyl propanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenyl propanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

Esters of araliphatic alcohols and aliphatic carboxylic acids such as benzyl acetate; benzyl propionate; benzyl isobutyrate; benzyl isovalerianate; 2-phenyl ethyl acetate; 2-phenylethyl propionate; 2-phenylethyl isobutyrate; 2-phenylethyl iso-valerianate; 1-phenylethyl acetate; alpha-trichloromethyl benzyl acetate; alpha,alpha-dimethylphenyl ethyl acetate; alpha,alpha-dimethylphenyl ethyl butyrate; cinnamyl acetate; 2-phenoxyethyl isobutyrate; 4-methoxybenzyl acetate;

Araliphatic ethers such as 2-Phenylethyl methyl ether; 2-phenylethyl isoamyl ether; 2-phenylethyl-1-ethoxyethyl ether; phenylacetaldehyde dimethylacetal; phenylacetaldehyde diethylacetal; hydratropaaldehyde dimethylacetal; phenylacetaldehydeglycerolacetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

Aromatic and araliphatic aldehydes such as benzaldehyde; phenylacetaldehyde; 3-phenylpropanal; hydratropaaldehyde; 4-methylbenzaldehyde; 4-methylphenyl acetaldehyde; 3-(4-ethylphenyl)-2,2-dimethylpropanal; 2-methyl-3-(4-isopropyl phenyl) propanal; 2-methyl-3-(4-tert.-butylphenyl)propanal; 2-methyl-3-(4-isobutyl phenyl) propanal; 3-(4-tert.-butylphenyl)propanal; cinnamaldehyde; alpha-butyl cinnamaldehyde; alpha-amyl cinnamaldehyde; alpha-hexyl cinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

Aromatic and araliphatic ketones such as acetophenone; 4-methylaceto phenone; 4-methoxyacetophenone; 4-tert-.butyl-2,6-dimethylacetophenone; 4-phenyl-2-butanone; 4-(4-hydroxyphenyl)-2-butanone; 1-(2-naphthalenyl)ethanone; 2-benzofuranyl ethanone; (3-methyl-2-benzofuranyl) ethanone; benzophenone; 1,1,2,3,6-hexamethyl-5-indanyl methyl ketone; 6-tert.butyl-1,1-dimethyl-4-indanyl methyl ketone; 1[2,3-dihydro-1,1,2,6-tetramethyl-3-(1-methylethyl)-1H-5-indenyl] ethanone; 5',6',7',8'-tetrahydro-3',5',5',6',8',8'-hexamethyl-2-acetonaphthone;

Aromatic and araliphatic carboxylic acids and their esters such as benzoic acid; phenylacetic acid; methyl benzoate; ethyl benzoate; hexyl benzoate; benzyl benzoate; methyl phenyl acetate; ethyl phenyl acetate; geranyl phenyl acetate; phenyl ethyl phenyl acetate; methyl cinnamate; ethyl cinnamate; benzyl cinnamate; phenyl ethyl cinnamate; cinnamyl cinnamate; allyl phenoxy acetate; methyl salicylate; isoamyl salicylate; hexyl salicylate; cyclohexyl salicylate; cis-3-hexenyl salicylate; benzyl salicylate; phenyl ethyl salicylate; methyl 2,4-dihydroxy-3,6-dimethylbenzoate; ethyl 3-phenyl glycidate; ethyl 3-methyl-3-phenyl glycidate;

Nitrogen-containing aromatic compounds such as 2,4,6-trinitro-1,3-dimethyl-5-tert-butylbenzene; 3,5-dinitro-2,6-dimethyl-4-tert.butylacetophenone; cinnamic acid nitrile; 3-methyl-5-phenyl-2-pentenoic acid nitrile; 3-methyl-5-phenylpentanoic acid nitrile; methyl anthranilate; methyl N-methyl anthranilate; Schiff bases of methyl anthranilate with 7-hydroxy-3,7-dimethyloctanal, 2-methyl-3-(4-tert.-butylphenyl)propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; scatole; 2-methoxy-3-isopropylpyrazine; 2-isobutyl-3-methoxypyrazine;

Phenols, phenyl ethers and phenyl esters such as estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenyl acetate;

Heterocyclic compounds such as 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

Lactones such as 1,4-octanolide; 3-methyl-1,4-octanolide; 1,4-nonanolide; 1,4-decanolide; 8-decene-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecene-1,15-olide; cis- and trans-12-pentadecene-1,15-olide; 1,16-hexadecanolide; 9-hexadecene-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin;

and any mixtures of the abovementioned perfumes or flavourings.

In a second aspect, the present invention relates to a process for the preparation of a compound of general formula (I), formula (II) or formula (III) or a mixture comprising one, two or three compounds selected from the group consisting of compounds of general formula (I), formula (II) and formula (III), which comprises the steps of:

(a) esterification of itaconic acid with an alcohol selected from the group consisting of an aliphatic, araliphatic or aromatic alcohol having 1 to 10 carbon atoms or a polyol having 2 to 6 hydroxyl groups to obtain an itaconic acid diester; and (b) Isomerization of the itaconic diester with an organic nitrogenous base to obtain a compound of the general formula (I), formula (II) or formula (III) or a mixture comprising one, two or three compounds selected from the group consisting of compounds of the general formula (I), formula (II) and formula (III).

The process for the preparation of a compound of the general formula (I), formula (II) or formula (III) or a mixture comprising one, two or three compounds selected from the group consisting of compounds of the general formula (I), formula (II) and formula (III) is described in more detail with reference to the illustration of the performance of the process in FIG. 1.

In the first reaction step (step (a)) of the process according to the invention, itaconic acid is esterified with an approximately equimolar amount or excess of alcohol. The reaction is acid catalyzed, preferably using sulfuric acid or p-toluenesulfonic acid, under reflux. Unreacted alcohol is then distilled off. In this process, the diester of itaconic acid is obtained. The acid-catalyzed esterification step of the itaconic acid takes place according to conventional process conditions known to a person skilled in the art.

In the second step (step (b)) of the process according to the invention, the itaconic acid diester obtained in the first step is isomerized using an organic nitrogenous base to obtain one or more of the compound(s) selected from the group consisting of compounds of general formula (I), formula (II) and/or formula (III) in general, or to obtain one or more of the compound(s) selected from the group consisting of diesters of mesaconic acid, citraconic acid and/or itaconic acid in particular.

This isomerization reaction is preferably carried out in a solvent and requires temperatures of 100 to 150° C. Here, too, the solvent is subsequently removed.

Particularly preferred in this respect, according to a further development of the invention, is the method of preparation in which a high-boiling solvent is used in step (b).

The high boiling solvent preferably contains solvents with a boiling point higher than 250° C., even more preferably higher than 300° C. Polyalkylene glycol (PAG)-based products have proven themselves here. Such are, for example, Synalox® 50-B SYNALOX™ 50-xB, which are known as lubricants, and are alcohol-containing materials containing oxyethylene and oxypropylene groups with a single terminal hydroxyl group having the structure: RO—[$CH_2$—C($CH_3$)HO]$_{n-}$[$CH_2$CH2O]$_{m-H}$.

In an alternative and preferred further development of the invention, in step (b) a solvent system is used as a protective solvent comprising a high boiling solvent having a boiling point higher than 150° C. and further comprising a co-solvent having a boiling point of between 90° C. and 120° C. This system significantly increases the yield, because without the protective solvent, the distilled product tends to polymerize at volume scale with larger reaction vessels on the longer distillation path. It was shown that even with larger batch sizes, the yield could be increased, or remain high, if the protective solvent has a boiling point such that it can also be co-distilled with the product to prevent polymerization of the product during distillation. Particularly preferably, the co-solvent has a boiling point of between 95° C. and 110° C., more preferably between 100° C. and 105° C.

The protective solvent or the co-solvent can be separated after the distillation step by common methods.

Suitable protective solvents or co-solvents are:

aliphatic hydrocarbons, and in particular paraffins, preferably octane, isooctane, nonane, decane, undecane or tetradecane;

aromatic hydrocarbons, preferably toluene, xylenes, ethylbenzenes, diethylbenzenes, trimethylbenzenes, cumen, pseudocumen or petroleum fractions consisting of a mixture of alkylbenzenes, in particular the fractions of the Solvesso® type;

chlorinated aliphatic hydrocarbons, preferably 1,1,2-trichloroethane, pentachloroethane, 1-iodo-2-methyl-propane, 1-chlorohexane or 1-chloro-2-ethyl hexane;

chlorinated aromatic hydrocarbons, preferably chlorobenzenes or chlorotoluenes;

Ethers, in particular aliphatic ethers, preferably butyl ether, isobutyl ether, ethyl hexyl ether, 1-butoxy-2-methoxyethane, 1,1-diethoxybutane, amyl ether, isoamyl ether or dipropoxymethane;

aromatic ethers, preferably phenylpropyl ether or mesityl oxide;

nitrated compounds, preferably nitropropane or nitrobenzene;

aliphatic, cycloaliphatic or aromatic ketones, preferably methyl ethyl ketone, methyl isobutyl ketone, diisobutyl ketone, methyl n-amyl ketone, methyl isoamyl ketone, cyclohexanone, methyl cyclohexanone or diacetone alcohol.

Protective solvents or co-solvents can also be used as a separate mixture.

A solvent system consisting of the high-boiling solvent polyalkylene glycol (PAG) and the co-solvent dioxane has proven to be particularly advantageous.

For esterification, i.e. for the preparation of the itaconic acid diester, aliphatic, araliphatic or aromatic alcohols having 1 to 10 carbon atoms or polyols having 2 to 6 hydroxyl groups, preferably diols thereof, are used in step (a) of the process according to the invention.

Preferably, methanol, isopropyl alcohol, isomeric butanol, ethylene glycol, diethylene glycol, propylene glycol, dipropylene glycol or glycerol are used to prepare the itaconic acid diester. Most preferably, methanol, ethanol or propanol are used for esterification of itaconic acid. The use of a combination, i.e. a mixture of methanol, ethanol and/or propanol for esterification is also possible.

The isomerization of the diester of itaconic acid to the compounds of the general formulae (I), (II) and (III), in particular to the diesters of mesaconic acid, ctraconic acid and itaconic acid, in step (b) of the process according to the invention takes place using an organic nitrogen-containing base as catalyst.

The organic nitrogen-containing base is selected from the group consisting of TMEDA (N, N, N', N'-tetramethylethylenediamine) (boiling point: 121° C.), TEA (tetraethylamine) (boiling point: 89° C.), dibutylamine (boiling point: 159.6° C.), pyridine (boiling point: 115° C.), NMP (N-methyl-2-pyrrolidone) (boiling point: 202° C.), trioctylamine (boiling point: 365° C.) and mixtures of the above compounds.

An advantage of isomerization with an organic nitrogen-containing base is that the N-base can be well separated from the products, i.e. the compounds of the general formula (I), formula (II) or formula (III), due to different boiling points after isomerization. The separation of the N-base from the products or the recovery of the N-base in the process according to the invention is carried out by distillation. After distillation, the N-base can be used again in the process according to the invention. The organic nitrogen-containing bases used in the process according to the invention have the further advantage that they do not adversely affect the odour or taste profile of the products obtained.

Isomerization of the itaconic acid diester using TMEDA or triethylamine has proven to be particularly advantageous. As an isomerization comparison shows, isomerization with one of the two organic nitrogenous bases gives particularly high yields compared to isomerization with the classical ruthenium catalyst, with a simultaneous reduction in reaction time, as can be seen in Table 1 below:

TABLE 1

| | Rutenium-Catalyst | Triethylamine | TMEDA | n-Benzyl dimethylamine |
|---|---|---|---|---|
| Response time (h) | 6-12 | 5-6 | 2 | 2 |
| Reaction temperature ° C.) | 180 | 114 | 130 | 130 |
| Catalyst quantity (based on the reactant (% by weight)) | 0.70 | 44 | 10 | 10 |

TABLE 1-continued

| | Rutenium-Catalyst | Triethylamine | TMEDA | n-Benzyl dimethylamine |
|---|---|---|---|---|
| Analysis according to GC after end of reaction | 25% Educt 75 Product (6% cis/ 69% trans) | 26% Educt 72% Product (2% cis/ 70% tans) | 28% Educt 71% Product (3% cis/ 68% trans) | 68% Educt 32% Product (2% cis/ 30% trans) |
| Yield after distillation (%) | Approx. 50% | 90% | 97% | — |

As can be further seen from Table 1, the isomerization of the itaconic acid diester using TMEDA has been found to be particularly advantageous due to its different boiling point and thus its ease of separation from the compounds of general formula (I), formula (II) or formula (III). With the use of TMEDA, the reaction time of the isomerization of the itaconic acid diester can also be significantly reduced and, moreover, leads to the best results as far as the mixing ratios of the compounds of the general formulae (I), (II) and (III) to one another are concerned, as described in detail below.

The isomerization of the itaconic diester in step (b) of the process according to the invention is carried out for a period of 1 to 5 hours in order to obtain an optimal isomerization of the itaconic diester to the compounds of general formulae (I), (II) and (III). Preferably, the isomerization is carried out for a period of 2 to 3 hours.

The process according to the present invention results in isomer mixtures or fragrance or flavor mixtures in which the compound of formula (I), is present in an amount of at least 50 to 100% by weight, even more preferably from 60 to 78% by weight and most preferably from about 66 to 72% by weight, the compound of formula (II) is present in an amount of at least 2 to 8% by weight, even more preferably from 3 to 7% by weight and most preferably from 4 to 6% by weight, and the compound of formula (III) is present in an amount of at least 18 to 31% by weight, even more preferably from 20 to 29% by weight and most preferably from 20 to 29% by weight.% by weight and particularly preferably from 4 to 6% by weight, and the compound of the formula (III) is present in an amount of at least from 18 to 31% by weight, still more preferably from 20 to 29% by weight and most preferably from 22 to 27% by weight, based on the sum of the compounds of the general formula (I), formula (II) and formula (III) or based on the total weight of the isomer mixture.

The above mixing ratios also apply to the compound mixtures of the respective particularly preferred dimethyl esters, diethyl esters, dipropyl esters or dibutyl esters, in particular diethyl esters, mesaconic acid, citraconic acid and itaconic acid.

In a preferred variant of the process according to the present invention, the compound of formula (I) is present in a ratio of 3 to 1, preferably in a ratio of 2.5:1, even more preferably in a ratio of 1.5:1, to the sum of the two compounds of formula (II) and formula (III) in the fragrance or flavour mixture. These ratios also apply to the compound mixtures of the respective preferred dimethyl esters, diethyl esters, dipropyl esters or dibutyl esters, in particular diethyl esters, of mesaconic acid, citraconic acid and itaconic acid. Higher proportions of the mesaconic acid esters result in a stronger pear odor.

The process according to the invention furthermore leads to a compound of the general formula (I) or to a fragrance or flavour mixture comprising the compound of the general formula (I), in particular the respective dimethyl esters, diethyl esters, dipropyl esters or dibutyl esters of mesaconic acid, in at least 98.0% purity, but preferably also in 100.0% purity. Such a fragrance or flavour mixture with pure or almost pure mesaconic acid dieters, in particular mesaconic acid diethyl esters, exhibits a particularly strong odour with a pear note.

A preferred embodiment of the process according to the present invention also relates to a process for preparing a compound (E)-2-methylbut-2-endicarboxylic acid diester (mesaconic acid diester), (Z)-2-methylbut-2-endicarboxylic acid diester (citraconic acid diester) or 2-methylenebutanedicarboxylic acid diester (itaconic acid diester) or for preparing a mixture, comprising one, two or three compounds selected from the group consisting of (E)-2-methylbut-2-endicarboxylic acid diester (mesaconic acid diester), (Z)-2-methylbut-2-endicarboxylic acid diester (citraconic acid diester), and 2-methylenebutanedicarboxylic acid diester (itaconic acid diester), which comprises the steps of:

(a) esterification of itaconic acid with an alcohol selected from the group consisting of methanol, ethanol, propanol and butanol to obtain an itaconic acid diester; and (b) isomerization of the itaconic acid diester with an organic nitrogen-containing base to obtain a compound (E)-2-methylbut-2-endicarboxylic acid diester (mesaconic acid diester), (Z)-2-methylbut-2-endicarboxylic acid diester (citraconic acid diester) or 2-methylenebutanedicarboxylic acid diester (itaconic acid diester) or a mixture, comprising one, two or three compounds selected from the group consisting of (E)-2-methylbut-2-endicarboxylic acid diester (mesaconic acid diester), (Z)-2-methylbut-2-endicarboxylic acid diester (citraconic acid diester), and 2-methylenebutanedicarboxylic acid diester (itaconic acid diester).

In a most preferred variant, the diesters of mesaconic acid, citraconic acid and/or itaconic acid obtained in the above-described process according to the general formulae (I), (II) and (III) are diethyl esters, namely diethyl (E)-2-methylbut-2-endioate, diethyl (Z)-2-methylbut-2-endioate or diethyl-2-methylene-butanedioate or mixtures comprising one, two or three compounds from the group consisting of diethyl (E)-2-methylbut-2-endioate, diethyl (Z)-2-methylbut-2-endioate and diethyl-2-methylene-butanedioate.

In this variant, the process according to the invention results in a mixture of isomers or a mixture of fragrances or flavours, in which diethyl (E)-2-methylbut-2-endioate or mesaconic acid diethyl ester (compound of formula (I)) is present in an amount of at least 50 to 100% by weight, still more preferably of 60 to 78% by weight, most preferably of 66 to 72% by weight.%, more preferably from 60 to 78%, most preferably from 66 to 72% by weight, diethyl (Z)-2-methylbut-2-endioate (compound of formula (II)) in an amount of at least from 2 to 8% by weight, more preferably from 3 to 5% by weight, or a mesaconic acid diethyl ester (compound of formula (I)).% by weight, more preferably from 3 to 7% by weight and most preferably from 4 to 6% by weight, and diethyl 2-methylene butanedioate (compound of formula (III)) is present in an amount of at least from 18 to 31% by weight, more preferably from 20 to 29% by weight and most preferably from 22 to 27% by weight, based on the sum of the compounds of the general formula (I), formula (II) and formula (III) or based on the total weight of the isomer mixture.

Compared to the process according to WO 2018/114073 A1, the process according to the present invention is characterized by comprising fewer, i.e. only two, and shorter synthesis steps, i.e. the total reaction time is shorter.

A further advantage of the process according to the invention is that the isomerization of the diesters of itaconic acid is carried out without using a halogen, in particular iodine, but using an organic nitrogen-containing base. Moreover, the use of an organic nitrogen-containing base is not odorous.

In contrast, the use of iodine as a catalyst in the isomerization of the citraconic acid esters into the mesaconic acid esters and itaconic acid esters in the prior art process requires a high amount of iodine to fully complete the isomerization reaction. This in turn requires an additional step of purification of the resulting product to separate excess iodine from the reaction mixture. The use of iodine further leads to accumulations on double bonds, which in turn requires subsequent dehydrohalogenation.

As can be seen from Example 1 below, the large-scale production of the fragrance or flavouring mixtures results in a higher iodine content in the final product, due to the larger amounts of iodine. In contrast, the large-scale production of the fragrance or flavouring mixture according to the present invention results in iodine-free end products. Therefore, the process according to the present invention is particularly advantageous.

In addition, the fragrance or flavoring compositions produced by the prior art process are not free of impurities and by-products. Some of these impurities and by-products are undesirable because they have an adverse effect on the fragrance compounds. For example, the fragrance or flavorant mixtures contain halogen, particularly iodine, which is used in the synthesis.

Such impurities of iodine are not present in the fragrance or flavour mixtures prepared by the process according to the invention, since the synthesis does not involve the use of halogen, in particular iodine.

The process according to the present invention has the further advantage of providing higher yields compared to the process according to WO 2018/114073 A1. The yields in the process according to the present invention are >90%, preferably >97%. In contrast, the yields in the process according to WO 2018/114073 A1 are about 60%. Moreover, unreacted starting material can be used in a further synthesis process.

The above-mentioned advantages of the process according to the invention thus contribute to the fact that the fragrances or flavourings or fragrance or flavouring mixtures with a fruity, pear-like aroma can be produced with less technical effort, i.e. with fewer synthesis steps, and thus at lower cost with high purity.

In a further, third aspect, the present invention relates to fragrances of the general formula (I), formula (II) or formula (III) or a fragrance or flavour mixture comprising one, two or three compound(s) from the group consisting of compounds of the general formula (I), formula (II) and formula (III) obtainable by the process according to the invention, the process being particularly characterized in that it is carried out without the use of halogen-containing, in particular iodine-containing, reagents.

Surprisingly, it has been found that the mixture of isomers of the compounds of formula (I), formula (II) and/or formula (III) in general and the mesaconic diesters of general formula (I), preferably the mesaconic diethyl esters, in particular, are eminently suitable for imparting, modifying and/or enhancing a pear-like fragrance or flavor.

A fourth aspect of the invention therefore relates to a method of imparting, modifying or enhancing a fruity, pear-like odor note in a fragrance blend, perfume oil, cosmetic composition, applicator or detergent and cleaning composition, or of imparting, modifying or enhancing a fruity, pear-like flavor note in a food, animal feed or pharmaceutical product, comprising the steps of:

(i1) providing the fragrance or flavour mixture of the invention comprising the compounds of general formula (I), formula (II) and formula (III); and (i2) mixing a sensory effective amount of the fragrance or flavour mixture sufficient to elicit a fruity, pear-like odour or flavour in the finished preparation with at least one further fragrance or flavour or a mixture of further fragrances or flavours;

or (ii1) providing a fragrance or flavour mixture according to the invention, comprising the compounds of general formula (I), formula (II) and formula (III); and (ii2) mixing a sensory effective amount of the fragrance or flavour mixture sufficient to produce a fruity, pear-like odour or flavour in the finished preparation with a perfume oil, cosmetic, applicator, detergent, food, animal feed or pharmaceutical product.

A mixture of (E)-2-methyl-but-2-endicarboxylic diesters (mesaconic diesters), (Z)-2-methyl-but-2-endicarboxylic diesters (citraconic diesters) and 2-methylenebutanedicarboxylic diesters (itaconic diesters) is preferred. This applies in particular to the respective mixtures of the particularly preferred dimethyl esters, diethyl esters, dipropyl esters or dibutyl esters.

Most preferred, therefore, in the method for imparting, modifying or enhancing a fruity, pear-like odor or flavor is a mixture of diethyl (E)-2-methylbut-2-endioate, diethyl (Z)-2-methylbut-2-endioate and diethyl 2-methylene butanedioate.

Another aspect of the invention relates to the use of a sensory effective amount of the fragrance or flavour mixture of the invention comprising the compounds of formula (I), formula (II) and formula (III) in general, or comprising diethyl (E)-2-methylbut-2-endioate (mesaconic acid diethyl ester) in admixture with diethyl (Z)-2-methylbut-2-endioate and diethyl 2-methylene butanedioate in particular, for imparting, modifying or enhancing a fruity, pear-like odor or flavor note in a perfume blend, perfume oil, cosmetic agent, applicator, detergent and cleaning agent, foodstuff, animal feed or pharmaceutical product or for the preparation of a perfume blend, perfume oil, cosmetic agent, applicator, detergent and cleaning agent, foodstuff, animal feed or pharmaceutical product.

Due to its advantageous olfactory properties, the fragrance or flavouring mixtures according to the invention are ideally suited for fragrancing or perfuming or for flavouring products with a pear note.

With regard to preferred input materials and input quantities, reference is made to the above explanations, which are included here, so that it is unnecessary to repeat them.

Preferred for this purpose are fragrance or flavour mixtures generally comprising the compounds of formula (I), formula (II) and formula (III). Even more preferred are fragrance or flavoring mixtures of (E)-2-methyl-but-2-endicarboxylic acid diesters (mesaconic acid diesters), (Z)-2-methyl-but-2-endicarboxylic acid diesters (citraconic acid diesters) and 2-methylenebutanedicarboxylic acid diesters (itaconic acid diesters), this applies in particular to the mixtures of the respective dimethyl esters, diethyl esters, dipropyl esters or dibutyl esters of mesaconic acid, itaconic acid and itaconic acid.

The best results for fragrancing or flavouring products are obtained with a fragrance or flavouring mixture of diethyl (E)-2-methylbut-2-endioate or mesaconic acid diethyl ester with diethyl (Z)-2-methylbut-2-endioate and diethyl 2-methylene butanedioate.

In particular, it is again emphasized that the respective particularly preferred variants and further embodiments of any embodiments of the present invention refer to an isomer mixture of diethyl (E)-2-methylbut-2-endioate (mesagonic acid diethyl ester), diethyl (Z)-2-methylbut-2-endioate (citraconic acid diethyl ester) and diethyl 2-methylene-butanedioate (itaconic acid diethyl ester) containing these compounds in an amount of at least 50% by weight in total.

Ultimately, the present invention relates to fragrance mixtures, perfume oils, cosmetic agents, application agents, detergents and cleaning agents, foodstuffs, animal feedstuffs or pharmaceutical products which contain the fragrance or flavour mixture according to the invention in a sensory effective amount.

These perfume mixtures or perfume oils, cosmetic compositions, application compositions, detergents and cleaning compositions, foodstuffs or animal feeds, or their further ingredients or compositions, are preferably those as described in detail in paragraphs [0074] to [0204] of WO 2018/114073 A1. This disclosure is incorporated by specific reference in its entirety in the present application.

An application agent is understood to mean all agents mentioned herein which do not fall under the group of perfume oils, cosmetic agents or detergents and cleaning agents.

In these perfume mixtures, compositions and foodstuffs, according to a preferred further development of the invention, the perfume or flavour mixture according to the present invention is present in amounts of 0.05 to 5% by weight, based on the perfume mixture, composition or foodstuff, respectively.

The invention therefore relates to perfume mixtures or perfume oils, cosmetic compositions, application compositions, detergents and cleaning compositions, foodstuffs and also animal feedstuffs which contain the perfume or flavour mixture according to the invention, which comprises the compounds of the general formula (I), formula (II) and formula (III) in general, or the diethyl (E)-2-methylbut-2-endioate or mesaconic acid diethyl ester in admixture with diethyl (Z)-2-methylbut-2-endioate and diethyl 2-methylene-butanedioate in particular.

Preferably, the fragrance or flavor mixtures according to the invention are combined with further ingredients. Preferred further ingredients are selected from the group consisting of:

Preservatives, preferably those mentioned in US 2006/0089413, abrasives, anti-acne agents and sebum reducing agents, preferably those mentioned in WO 2008/046791, anti-aging agents, preferably those mentioned in WO 2005/123101, antibacterial agents, anticellulite agents, anti-dandruff agents, preferably those mentioned in WO 2008/046795, anti-inflammatory agents, anti-irritants (anti-inflammatory, anti-irritant and anti-irritant agents), preferably those mentioned in WO 2007/042472 and US 2006/0089413, antimicrobial agents, preferably those mentioned in WO 2005/123101, antioxidants, preferably those mentioned in WO 2005/123101, astringents, antiseptic agents, antistatic agents, binders, buffers, carriers, preferably those mentioned in WO 2005/123101, chelating agents, preferably those mentioned in WO 2005/123101, cell stimulants, cleansing agents, conditioning agents, depilatories, surfactants, deodorants and antiperspirants, preferably those mentioned in WO 2005/123101, emollients, emulsifiers, preferably those mentioned in WO 2005/123101, enzymes, essential oils, preferably those mentioned in US 2008/0070825, insect repellents, preferably those mentioned in WO 2005/123101, fibers, film formers, fixatives, foaming agents, foam stabilizers, anti-foaming substances, foam boosters, fungicides, gelling agents and gelling agents, preferably those mentioned in WO 2005/123101, hair care agents, hair shaping agents, hair smoothing agents, moisture regulators (moisturizing, moistening and/or moisture retaining substances), preferably those mentioned in WO 2005/123101, osmolytes, preferably those mentioned in WO 2005/123101, compatible solutes, preferably those mentioned in WO 01/76572 and WO 02/15686, bleaching agents, strengthening agents, stain removing agents, optically brightening agents, impregnating agents, soil-repellent agents, friction-reducing agents, lubricants, moisturizers, ointments, opacifiers, plasticizing agents, covering agents, polishes, brighteners, polymers, preferably those mentioned in WO 2008/046676, powders, proteins and protein hydrolysates, preferably those mentioned in WO 2005/123101 and WO 2008/046676, refatting agents, abrasive agents, skin-soothing agents, skin-cleansing agents, skin-caring agents, skin repair agents, preferably containing cholesterol and/or fatty acids and/or ceramides and/or pseudoceramides, preferably those mentioned in WO 2006/053912, skin lightening agents, preferably those mentioned in WO 2007/110415, skin protecting agents, skin softening agents, skin cooling agents, preferably those mentioned in WO 2005/123101, skin warming agents, preferably those mentioned in WO 2005/123101, stabilizers, UV absorbing agents and UV filters, preferably the benzylidene beta-dicarbonyl compounds mentioned in WO 2005/123101, preferably the alpha-benzoyl cinnamic acid nitriles mentioned in WO 2005/107692, preferably the AhR receptor antagonists mentioned in WO 2006/015954, preferably those mentioned in WO 2007/128723 and WO 2007/060256, detergents, fabric softeners, suspending agents, skin tanning agents, preferably those mentioned in WO 2006/045760, thickening agents, vitamins, preferably those mentioned in WO 2005/123101, oils, waxes and fats, preferably those mentioned in WO 2005/123101, phospholipids, preferably those mentioned in WO 2005/123101, fatty acids (saturated fatty acids, mono- or polyunsaturated fatty acids, $\alpha$-hydroxy acids, polyhydroxy fatty acids), preferably those mentioned in WO 2005/123101, liquefiers, colorants and color-protecting agents as well as pigments, preferably those mentioned in WO 2005/123101, anticorrosives, aromas and flavors as well as further additional fragrances, preferably those mentioned in S. Arctander, Perfume and Flavor Chemicals, self-published, Montclair, N.J., 1969 and Surburg, Panten, Common Fragrance and Flavor Materials, 5th Edition, Wiley-VCH, Weinheim 2006, in particular the further fragrances explicitly mentioned in US 2008/0070825 which are not already components of the perfume oil mixture according to the invention, alcohols and polyols, preferably those mentioned in WO 2005/123101, surfactants, preferably those mentioned in WO 2005/123101, animal extracts, yeast extracts, extracts of algae or microalgae, electrolytes, liquefiers, organic solvents, preferably those mentioned in WO 2005/

123101, or silicones and silicone derivatives, preferably those mentioned in WO 2008/046676.

The detergent or cleaning compositions containing the fragrance or flavoring mixture of compounds of the general formula (I), formula (II) and formula (III) according to the invention, or preferably a fragrance or flavoring mixture of diethyl (E)-2-methylbut-2-endioate, diethyl (Z)-2-methylbut-2-endioate and diethyl 2-methylene-butanedioate containing detergents and cleaning compositions (abbreviated as WSR compositions) within the meaning of the present invention may be in solid form as powders, granules, tablets and the like, but may also be in liquid, gel or paste form. Preferably, these are detergents suitable for both manual and machine washing, in particular of textiles. They may also be washing or cleaning compositions for the industrial sector or for the household sector. Cleaning agents may also be used, for example, for cleaning hard surfaces. They may be, for example, dishwashing detergents used for manual or machine cleaning of dishes. They may also be common industrial or household cleaners used to clean hard surfaces such as furniture surfaces, tiles, tiles, wall and floor coverings. In addition to tableware, hard surfaces may include all other hard surfaces, particularly those made of glass, ceramics, plastics or metal, in the home or industry.

The detergents and cleaning compositions (WSR agents) may have other commercially available ingredients, such as surfactants, builders, bleaching agents, bleach activators, thickeners, enzymes, electrolytes, pH adjusters, colorants and fragrances, foam inhibitors, antiredeposition agents, optical brighteners, graying inhibitors, wrinkle inhibitors, antimicrobial agents, preservatives, antioxidants, antistatics, UV adsorbers, heavy metal complexing agents, and the like.

In a preferred variant of the present invention, the perfume or flavoring mixtures or perfume oils, cosmetic compositions, application compositions and also the washing and cleaning compositions which have been prepared with the perfume or flavouring composition according to the invention, comprising a sensory effective amount of the compounds of the general formula (I), formula (II) and formula (III) or preferably with a fragrance mixture comprising a sensory effective amount of diethyl (E)-2-methylbut-2-endioate, diethyl (Z)-2-methylbut-2-endioate and diethyl 2-methylene butanedioate selected from the group consisting of: perfume extracts, eau de parfums, eau de toilettes, shaving waters, eau de colognes, pre-shave products, splash colognes, perfumed refreshing wipes, acidic, alkaline and neutral cleaning products such as floor cleaners, window glass cleaners, dishwashing detergents, bathroom and sanitary cleaners, scouring powders, solid and liquid WC cleaners, powder and foam carpet cleaners, liquid laundry detergents, powder laundry detergents, laundry pretreatment products, e.g. such as bleach, softeners and stain removers, fabric softeners, laundry soap, laundry tablets, disinfectants, surface disinfectants, air fresheners in liquid, gel or solid form, aerosol sprays, waxes and polishes such as furniture polishes, floor waxes, shoe polishes, personal care products such as solid and liquid soaps, shower gels, shampoos, shaving soaps, shaving foams, bath oils, cosmetic emulsions of the oil-in-water, water-in-oil and water-in-oil-in-water types, such as skin creams and lotions, facial creams and lotions, sun-creams and lotions, aftersun creams and lotions, hand creams and -lotions, foot creams and lotions, depilatory creams and lotions, aftershave creams and lotions, tanning creams and lotions, hair care products such as e.g. hair sprays, hair gels, hair lotions, hair conditioners, permanent and semi-permanent hair dyes, hair shaping products such as cold waves and hair straighteners, hair tonics, hair creams and lotions, deodorants and antiperspirants such as underarm sprays, roll-ons, deodorant sticks, deodorant creams, decorative cosmetic products, candles, lamp oils, incense, insecticides, repellents and propellants.

Particularly preferred perfume oils or compositions containing the perfume or flavoring mixture according to the invention are selected from the group consisting of:

- Eau de parfums, eau de toilettes, shaving waters (after-shave), eau de colognes, pre-shave products, splash colognes;
- Acidic, alkaline and neutral cleaning agents, especially in the household sector, preferably floor cleaners, window glass cleaners, dishwashing detergents, bathroom and sanitary cleaners, scouring agents, solid and liquid WC cleaners, powder and foam carpet cleaners, liquid detergents, powder detergents, fabric softeners, surface disinfectants, especially for hard surfaces (hard surface cleaner);
- Personal care products, preferably solid and liquid soaps, shower gels, shampoos, shaving soaps, shaving foams;
- cosmetic emulsions of the oil-in-water, water-in-oil and water-in-oil-in-water types, preferably skin creams and lotions, face creams and lotions, sunscreen creams and lotions, after-sun creams and lotions, hand creams and lotions, foot creams and lotions, depilatory creams and lotions, after-shave creams and lotions, skin tanning creams and lotions, skin whitening creams and lotions;
- Hair care products, preferably hair sprays, hair gels, setting hair lotions, hair conditioners, permanent and semi-permanent hair dyes, hair tonics, hair creams and lotions;
- Deodorants and antiperspirants, preferably underarm sprays, roll-ons (preferably as alcoholic or non-alcoholic solution, as gel or (micro)emulsion, deosticks (deodorant sticks), deodorant creams.

Particularly preferred perfumed compositions according to the invention are washing and cleaning compositions, hygiene or care products, in particular in the field of body and hair care, cosmetics and household.

In a preferred variant of the present invention, the foodstuffs flavoured with the flavouring mixture according to the invention, comprising a sensory effective amount of the compounds of general formula (I), formula (II) and formula (III) or preferably with a flavouring of diethyl (E)-2-methylbut-2-endioate, diethyl (Z)-2-methylbut-2-endioate and diethyl 2-methylene butanedioate, are selected from the group consisting of: Dairy products, beverages, candy, dietary supplements, dietary foods, food surrogates and semi-finished products, Furthermore, the flavoring mixtures according to the invention comprising a sensory effective amount of the compounds of general formula (I), formula (II) and formula (III) or preferably a flavoring mixture comprising a sensory effective amount of diethyl (E)-2-methylbut-2-endioate, diethyl (Z)-2-methylbut-2-endioate and diethyl 2-methylene butanedioate can also be used in the flavoring of pharmaceutical products.

Preferred products are those in which the proportion of the fragrance or flavoring mixture according to the invention in the product is 0.01 to 10% by weight, preferably 0.1 to 5% by weight and particularly preferably 0.25 to 3% by weight, in each case based on the total weight of the perfumed or flavored end product.

EXAMPLES

Example 1: Determination of the Iodine Content of Fragrance or Flavour Mixtures Prepared According to WO 2018/114073

The iodine content of the samples was determined according to EN 1511, CON-PV 01187, ICP-MS.
Sample 1: Iodine content: 23±4.6 mg/kg
Sample 2: Iodine content: 69±14 mg/kg
Sample 1 is a 3 kg batch process. Sample 2, on the other hand, is a 50 kg batch process. The higher the batch process, the more iodine is required, resulting in a higher iodine content in the final product.

Example 2: Preparation of Diethyl (E)-2-Methyl-but-2-Endioate, Diethyl (Z)-2-Methylbut-2-Endioate and Diethyl 2-Methylene Butanedioate

Step 1: Preparation of Diethyl 2-Methylene Butanedioate (Itaconic Acid Diethyl Ester)

Ethanol (2250 ml, 3% by volume) is placed in a 5-litre double jacketed flask and heated to 50° C. Then 2-methyl-enebutanoic acid (itaconic acid) (750 g, 5.76 mol, 1.0 equiv.) was added in portions until all dissolved. Sulfuric acid (126 ml, 0.4 equiv.) was then added and boiled at reflux for 5 hours. After completion of the reaction, excess ethanol was evaporated off at the rotary evaporator and the residue was diluted with MTBE (methyl tert-butyl ether) (150 ml) and washed successively with 5% NaCl solution (250 ml×2) and 5% Na2CO3 solution (250 ml). The resulting solution was dried over sodium sulfate. The resulting solution was evaporated at a temperature of 60° C. and a pressure of 500-10 mbar. Yield: 965.8 g; GC purity=99.9%.

Spectroscopic data of diethyl-2-methylene-butanedioate:

$^1$H NMR (400 MHz, $CDCl_3$) δ 6.32 (d, J=1.0 Hz, 1H), 5.70 (q, J=1.2 Hz, 1H), 4.22 (q, J=7.1 Hz, 2H), 4.16 (q, J=7.1 Hz, 2H), 3.33 (d, J=1.1 Hz, 2H), 1.30 (t, J=7.2 Hz, 3H), 1.26 (t, J=7.4 Hz, 3H).

$^{13}$C NMR (101 MHz, $CDCl_3$) δ 170.8, 166.2, 134.2, 128.1, 61.0, 60.1, 37.8, 14.2, 14.2.

Step 2: Preparation of Diethyl (E)-2-Methylbut-2-Endioate, Diethyl (Z)-2-Methylbut-2-Endioate and Diethyl 2-Methylene-Butanedioate A mixture of diethyl itaconic acid ester (500 g; 2.68 mol) with the nitrogen-containing base TMEDA (about 10% by weight; 50 g; 0.43 mol) was heated in a 2-liter three-neck flask at a temperature of 130 to 135° C. at atmospheric pressure for 2 to 4 hours. Gas chromatographic analysis gave a composition of 72% diethyl (E)-2-methylbut-2-ene dioate and diethyl (Z)-2-methylbut-2-endioate. The reaction mixture was then purified by distillation. First, TMEDA was distilled off at a temperature of 120° C. and a pressure of 1013 mbar (93% TMEDA was distilled off, which could be reused). Then, the obtained product mixture (diethyl (E)-2-methylbut-2-endioate, diethyl (Z)-2-methylbut-2-endioate and diethyl 2-methylene butanedioate) was further distilled at a temperature of about 224° C. and a pressure of 1013 mbar. Yield (mixture): 451 g; purity (mixture): >99%.

Spectroscopic data of the major isomer diethyl (E)-2-methylbut-2-endioate:

$^1$H NMR (400 MHz, CDCl3): δ=1.31 (t, J=7.1 Hz, 3H), 1.32 (t, J=7.2 Hz, 3H), 2.29 (d, J=1.5 Hz, 3H), 4.16 (q, J=7.5 Hz, 2H), 4.24 (m, 2H), 6.78 (d, J=1.6 Hz, 1H).

$^{13}$C NMR (101 MHz, $CDCl_3$): δ=167.2, 165.9, 143.8, 126.7, 61.6, 60.6, 14.3, 14.2, 14.1.

Example 3: Sensory Evaluation of the Fragrance or Flavour Mixture According to the Invention

TABLE 2

| Fragrances - Comparison | | |
|---|---|---|
| Pearadise | 10 ppm in Sugar solution | fruity,<br>pear-like,<br>slightly greasy and aldehydic,<br>weaker than ethyl decadienoate,<br>but more fruity and a bit soapy |
| Ethyl decadienoate-tr. cis-2,4 | 5 ppm in Sugar solution | Pear-like, fruity,<br>after peel,<br>after ester, juicy |
| Pear Flavor | 10 ppm in fruit base | pear, ester |
| Pear aroma (containing 1% ethyl decadienoate) | 10 ppm in fruit base | more bodies,<br>peel back<br>all in all more typical |
| Pear flavouring (contain 5% Pearadise) | 10 ppm in fruit base | more sweetness and body,<br>juicier,<br>natural |
| Aroma of red fruits | 15 ppm in fruit base | fruity, green,<br>after red fruits,<br>fruity strawberry note |
| Red fruit aroma (containing 0.001% Ethyl decadienoate) | 15 ppm in fruit base | juicier, more body |
| Aroma of red fruits (containing 0.005%) Pearadise) | 15 ppm in fruit base | even juicier,<br>nice body,<br>fuller, rounder taste,<br>more natural,<br>more authentic,<br>more raspberry |

TABLE 2-continued

| Fragrances - Comparison | | |
|---|---|---|
| Chocolate flavor | 0.25% in sweetened milk | |
| Chocolate flavouring (containing 0.005% ethyl decadienoate) | 0.25% in sweetened milk | fuller, rounder taste, slightly more chocolate-like, ethyl decadienoate dosage at the upper limit |
| Chocolate flavouring (containing 0.025% Pearadise) | 0.25% in sweetened milk | an even fuller taste, a little more body |

As can be seen from the results of the sensory evaluation in Table 2, the fragrance or flavour mixtures according to the invention in different carriers are characterised by a fuller, intense and fresh pear odour or flavour, which is qualitatively and quantitatively equivalent to or even exceeds the ethyl decadienoate standard, irrespective of the base material.

Example 4: Olfactometric Determination of the Odour Intensity of the Fragrance or Flavouring Mixture According to the Invention

TABLE 3

| Odour detection threshold (ODT) - comparison | |
|---|---|
| | Odour threshold value (ppm) |
| 2,4-trans-cis-ethyl decadienoate (Standard) | 0.0311 |
| Fragrance or flavour mixture according to the invention | 0.0356 |
| Mixture of fragrances or flavours (WO 2018/114073 A1) | 0.0474 |

The odor detection threshold (ODT) of the above samples was determined using a dynamic olfacometer with the designation TO8, in which an odorous air sample is diluted with clean air. The dilution is presented to the test subjects (testers) for evaluation. The device is operated with synthetic air from steel bottles or with treated compressed air. This clean air is used to operate two gas jet pumps which draw the sample air directly from a sample bag. The sample air is intensively mixed with the clean air in the gas jet pump. This mixture flows via a reversing valve to the individual sample places. The volume flow of the sample air is automatically adjusted by the control program by means of calibrated measuring orifices. The determination of the odour concentration is the most frequent application. Here, the sample air is presented for evaluation in ascending concentration until the odour is perceived by the test persons. At the first recognizable odor impression, a response button ("Yes, it smells") is pressed, and the odor threshold concentration is reached. The measurements, which are carried out with the olfactometer and with the participation of the test persons, are subject to fixed standards. These olfactometric measurement procedures are laid down in the European standard DIN EN 13725. The olfactometer TO8 and the measurement procedure implemented with it comply with these guidelines and make olfactometry an objective, generally accepted and proven measurement procedure.

As shown by the results of the olfactometric evaluation, the fragrance or flavor blend according to the present invention has an odor threshold comparable to that of the ethyl decadienoate standard, but a much lower odor threshold than the prior art fragrance or flavor blend.

Thus, the fragrance or flavorant mixtures according to the invention are excellently suited for fragrancing or flavoring. Due to the lower odor threshold value, smaller dosage amounts of the fragrance or flavoring mixture are sufficient to effect a perceptible fragrancing or flavoring.

The invention claimed is:

1. A method for preparing a compound of the general formula (I), formula (II) or formula (III)

Formula (I)

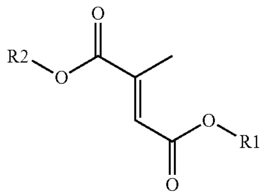

Formula (II)

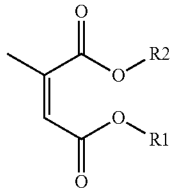

Formula (III)

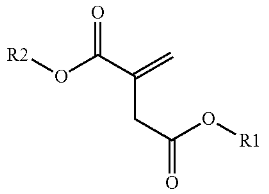

in which each R1 is selected from a linear, branched or cyclic alkyl radical having 1 to 10 carbon atoms, an araliphatic or aromatic radical, and in which each R2 is selected from a linear, branched or cyclic alkyl radical having 1 to 10 carbon atoms, an araliphatic or aromatic radical, or a mixture comprising one, two or three compound(s) from the group consisting of compounds of the general formula (I), formula (II) and formula (III), which comprises the following steps:

(a) esterification of itaconic acid with an alcohol selected from the group consisting of an aliphatic, araliphatic or aromatic alcohol having 1 to 10 carbon atoms and a polyol having 2 to 6 hydroxyl groups to obtain an itaconic acid diester; and (b) isomerization of the itaconic acid diester with an organic nitrogenous base to obtain a compound of the general formula (I), formula (II) or formula (III) or a mixture comprising one, two or three compounds selected from the group consisting of compounds of the general formula (I), formula (II) and formula (III).

2. The method of claim 1, wherein the alcohol is selected from the group consisting of methanol, isopropyl alcohol, isomeric butanol, ethylene glycol, diethylene glycol, propylene glycol, dipropylene glycol, glycerol and mixtures thereof and/or the organic nitrogen-containing base is selected from the group consisting of TMEDA (N,N,N',N'-tetramethylethylenediamine), TEA (tetraethylammonium), dibutylamine, pyridine, NMP (N-methyl-2-pyrrolidone), trioctylamine and mixtures thereof.

3. The method of claim 1, wherein the reaction time of step (b) is in a range of 1 to 5 hours.

4. The method of claim 1, wherein the compound of the general formula (I) is obtained in an amount from 50 by weight, the compound of the general formula (II) is obtained in an amount of 2 to 8% by weight, and the compound of the general formula (III) is obtained in an amount of 18 to 31% by weight, based on the sum of the compounds of the general formulae (I), (II) and (III).

5. A process for preparing a compound (E)-2-methyl-but-2-endicarboxylic acid diester (mesaconic acid diester), (Z)-2-methyl-but-2-endi-carboxylic acid diester (citraconic acid diester), or 2-methylenebutane-dicarboxylic acid diester (itaconic acid diester), or for preparing a mixture comprising one, two or three compounds selected from the group consisting of (E)-2-methyl-but-2-endi-carboxylic acid diester (mesaconic acid diester), (Z)-2-methyl-but-2-endi-carboxylic acid diester (citraconic acid diester), and 2-methylene-butane-dicarboxylic acid diester (itaconic acid diester) according to claim 1, which comprises the steps of:

(a) esterification of itaconic acid with an alcohol selected from the group consisting of methanol, ethanol, propanol and butanol to obtain an itaconic acid diester; and (b) isomerization of the itaconic acid diester with an organic nitrogen- containing base to obtain a compound (E)-2-methyl-but-2-endicarboxylic acid diester (mesaconic acid diester), (Z)-2-methyl-but-2-endicarboxylic acid diester (citraconic acid diester), or 2-methylene-butanedicarboxylic acid diester (itaconic acid diester), or a mixture, comprising one, two or three compounds selected from the group consisting of (E)-2-methyl -but-2-endicarboxylic acid diester (mesaconic acid diester), (Z)-2-methyl-but-2-endicarboxylic acid diester (citraconic acid diester), and 2-methylene-butanedicarboxylic acid diester (itaconic acid diester).

6. The process according to claim 1, characterized in that the diester of the mesaconic acid esters, citraconic acid esters and/or itaconic acid esters is a diethyl ester.

7. The method of claim 1, wherein the organic nitrogen-containing base is TMEDA.

* * * * *